US011117974B2

(12) United States Patent
Shirakawa

(10) Patent No.: US 11,117,974 B2
(45) Date of Patent: Sep. 14, 2021

(54) SPECIFICALLY PURIFIED ANTI-PRESEPSIN ANTIBODY

(71) Applicant: Mochida Pharmaceutical Co., Ltd., Tokyo (JP)

(72) Inventor: Kamon Shirakawa, Yokohama (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 559 days.

(21) Appl. No.: 15/754,451

(22) PCT Filed: Aug. 25, 2015

(86) PCT No.: PCT/JP2015/073839
§ 371 (c)(1),
(2) Date: Feb. 22, 2018

(87) PCT Pub. No.: WO2017/033281
PCT Pub. Date: Mar. 2, 2017

(65) Prior Publication Data
US 2018/0237537 A1 Aug. 23, 2018

(51) Int. Cl.
C07K 16/28 (2006.01)
C07K 7/06 (2006.01)
C07K 16/06 (2006.01)
G01N 33/53 (2006.01)
G01N 33/557 (2006.01)

(52) U.S. Cl.
CPC .......... C07K 16/2896 (2013.01); C07K 7/06 (2013.01); C07K 16/065 (2013.01); G01N 33/5306 (2013.01); G01N 33/557 (2013.01); C07K 2317/31 (2013.01); C07K 2317/92 (2013.01)

(58) Field of Classification Search
None
See application file for complete search history.

(56) References Cited

U.S. PATENT DOCUMENTS

| | | | |
|---|---|---|---|
| 7,465,547 B2 | 12/2008 | Furusako et al. | |
| 7,608,684 B2 | 10/2009 | Furusako et al. | |
| 7,901,900 B2 | 3/2011 | Furusako et al. | |
| 8,124,722 B2 | 2/2012 | Furusako et al. | |
| 2006/0068445 A1 | 3/2006 | Furusako et al. | |
| 2007/0106067 A1* | 5/2007 | Furusako ............ | A61P 37/02 530/388.22 |
| 2009/0029396 A1 | 1/2009 | Furusako et al. | |
| 2009/0203052 A1 | 8/2009 | Furusako et al. | |
| 2011/0086381 A1 | 4/2011 | Naito | |
| 2012/0309025 A1 | 12/2012 | Okamura et al. | |
| 2013/0337476 A1 | 12/2013 | Lee et al. | |
| 2015/0239982 A1* | 8/2015 | Shirakawa .......... | C07K 16/2896 530/387.3 |
| 2018/0201688 A1 | 7/2018 | Shirakawa | |

FOREIGN PATENT DOCUMENTS

| | | |
|---|---|---|
| EP | 2487489 B1 | 8/2015 |
| EP | 2251356 B1 | 3/2016 |
| EP | 2734550 B1 | 3/2017 |
| JP | 2005-106694 A | 4/2005 |
| WO | WO 2004/044005 A1 | 5/2004 |
| WO | WO2005/108429 * 11/2005 ............ C07K 14/70 |  |
| WO | WO 2005/108429 A1 | 11/2005 |
| WO | WO 2009/142303 A1 | 11/2009 |
| WO | WO 2011/093459 A1 | 8/2011 |
| WO | WO-2015/129774 A1 | 9/2015 |

OTHER PUBLICATIONS

Zou et al. (World J Emerg Med, 5(1): 16-19, 2014).*
Juan et al., "Identification of a Lipopolysaccharide Binding Domain in CD14 between Amino Acids 57 and 64," The Journal of Biological Chemistry, Mar. 10, 1995, 270(10):5219-5224.
Popov et al., "SCD14-ST (Presepsin) Level Monitoring in Cardiac Surgical Patients During Perioperative Period," Anesthesiology and Renimatology, 2003, 3:23-35, with English abstract.
Prokhorova, A.M., Ed., The Great Encyclopedic Dictionary, 1993, p. 858, definition of "kit" with English translation.
Yarilin, A.A., Principles of Immunology: Textbook, Moscow, Medicina, 1999, 172-174, with English translation.
Caldas et al., Mol. Immunol., May 2003, 39(15) :941-952.
Casset et al., "A peptide mimetic of an anti-CD4 monoclonal antibody by rational design," Biochemical and Biophysical Research Communications, 2003, 307:198-205.
Chien, N. C., et al., Proc. Natl. Acad. Sci. USA, 1989, vol. 84, No. 14, pp. 5532-5536.
De Pascalis et al., "Grafting of 'abbreviated' complementary-determining regions containing specificity-determining residues essentially for ligand contact to engineer a less immunogenic humanized monoclonal antibody," Journal of Immunology, 2002, 169:3076-3084.
Giusti et al., "Somatic diversification of S107 from an antiphosphocholine to an anti-DNA autoantibody is due to a single base change in its heavy chain variable region," Proceedings of the National Academy of Sciences, May 1987, vol. 84, pp. 2926-2930.
Gussow et al., "Humanization of Monoclonal Antibodies," Methods in Enzymology, 1991, 203:99-121.
Hayashi et al., "Increased Levels of Soluble CD14 in Sera of Periodontitis Patients," Infection and Immunity, Jan. 1999, 67(1):417-420.

(Continued)

Primary Examiner — Nelson B Moseley, II
(74) Attorney, Agent, or Firm — Foley & Lardner LLP

(57) ABSTRACT

The present invention provides anti-presepsin polyclonal antibodies specifically binding to a peptide comprising an amino acid sequence of SEQ ID NO: 1. As a result, anti-presepsin polyclonal antibodies which have less variation in measured values between lot-to-lot differences of antibodies compared to S68 antibodies and thus suitable anti-presepsin polyclonal antibodies for presepsin measurement are provided.

20 Claims, 3 Drawing Sheets
Specification includes a Sequence Listing.

(56) References Cited

OTHER PUBLICATIONS

Holm et al., "Functional mapping and single chain construction of the anti-cytokeratin 8 monoclonal antibody TS1," Molecular Immunology, 2007, 44:1075-1084.

Lawn et al., "Elevated serum concentrations of soluble CD14 in HIV– and HIV+ patients with tuberculosis in Africa: prolonged elevation during anti-tuberculosis treatment," Clinical & Experimental Immunology, 2000, 120:483-487.

MacCallum et al., "Antibody-antigen Interactions: Contact Analysis and Binding Site Topography," J. Mol. Biol., 1996, 262:732-745.

Mariuzza et al., "The Structural Basis of Antigen-Antibody Recognition," Ann. Rev. Biophys. Biophys. Chem., 1987, 16:139-159.

Rudikoff et al., "Single amino acid substitution altering antigen-binding specificity," Proc. Natl. Acad. Sci. USA, Mar. 1982, 79:1979-1983.

Vajdos et al., "Comprehensive Functional Maps of the Antigen-binding Site of an Anti-ErbB2 Antibody Obtained with Shotgun Scanning Mutanesis," J. Mol. Biol., Jul. 5, 2002, 320:415-428.

Winkler et al., "Changing the Antigen Binding Specificity by Single Point Mutations of an Anti-p24 (HIV-1) Antibody," J. Immunol., Oct. 15, 2000, 265:4505-4514.

Wu et al., "Humanization of a murine monoclonal antibody by simultaneous optimization of framework and CFR residues," Journal of Molecular Biology, Nov. 19, 1999, 294:151-162.

Yaegashi et al., "Evaluation of a newly identified soluble CD14 subtype as a marker for sepsis," Journal of Infection and Chemotherapy, 2005, 11:234-238.

Office Action dated Feb. 28, 2019, in corresponding Indonesian Patent Application No. P-00201605634, with English translation.

Okamura et al., "Development of a point-of-care assay system for measurement of presepsin (sCD14-ST)," Clinica Chimica Acta, 2011, vol. 412, pp. 2157-2161.

S. Ozhegov, $4^{th}$ Ed., Dictionary of the Russian Language, 2006, p. 375, definition of "kit".

Shirakawa et al., "Presepsin (sCD14-ST): development and evaluation of one-step ELISA with a new standard that is similar to the form of presepsin in septic patients," Clinical Chemistry and Laboratory Medicine, 2011, vol. 49, pp. 937-939.

Velkov V.V., "Presepsin is a novel highly effective biomarker of sepsis," Pediatriya, 2013, vol. 92, p. 128, with English translation.

Office Action dated Jun. 21, 2021 in Canadian Application No. 2,996,395.

Korean Office Action dated Jul. 19, 2021 in Korean Application No. 10-2016-7022978 with English machine translation.

\* cited by examiner

[Figure 1]
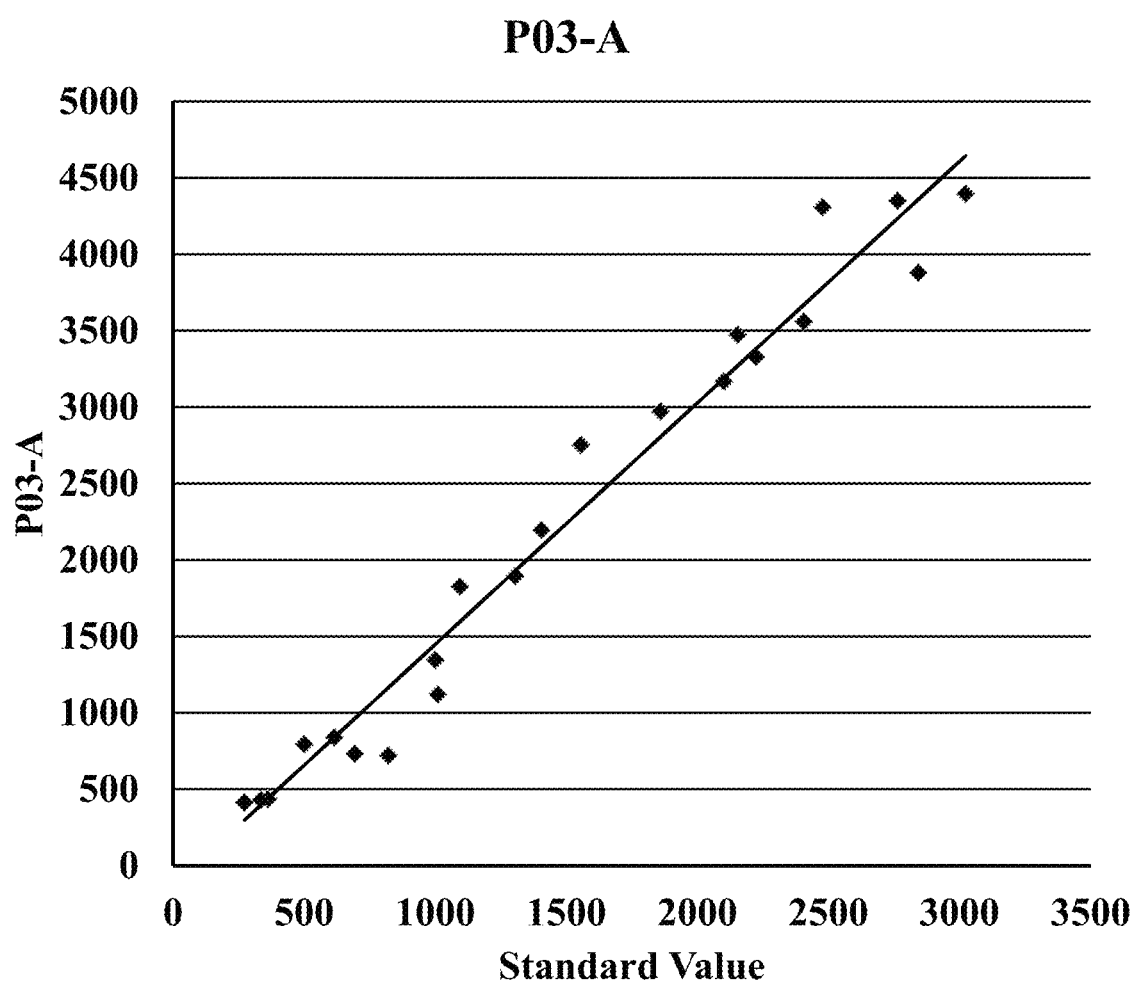

[Figure 2]
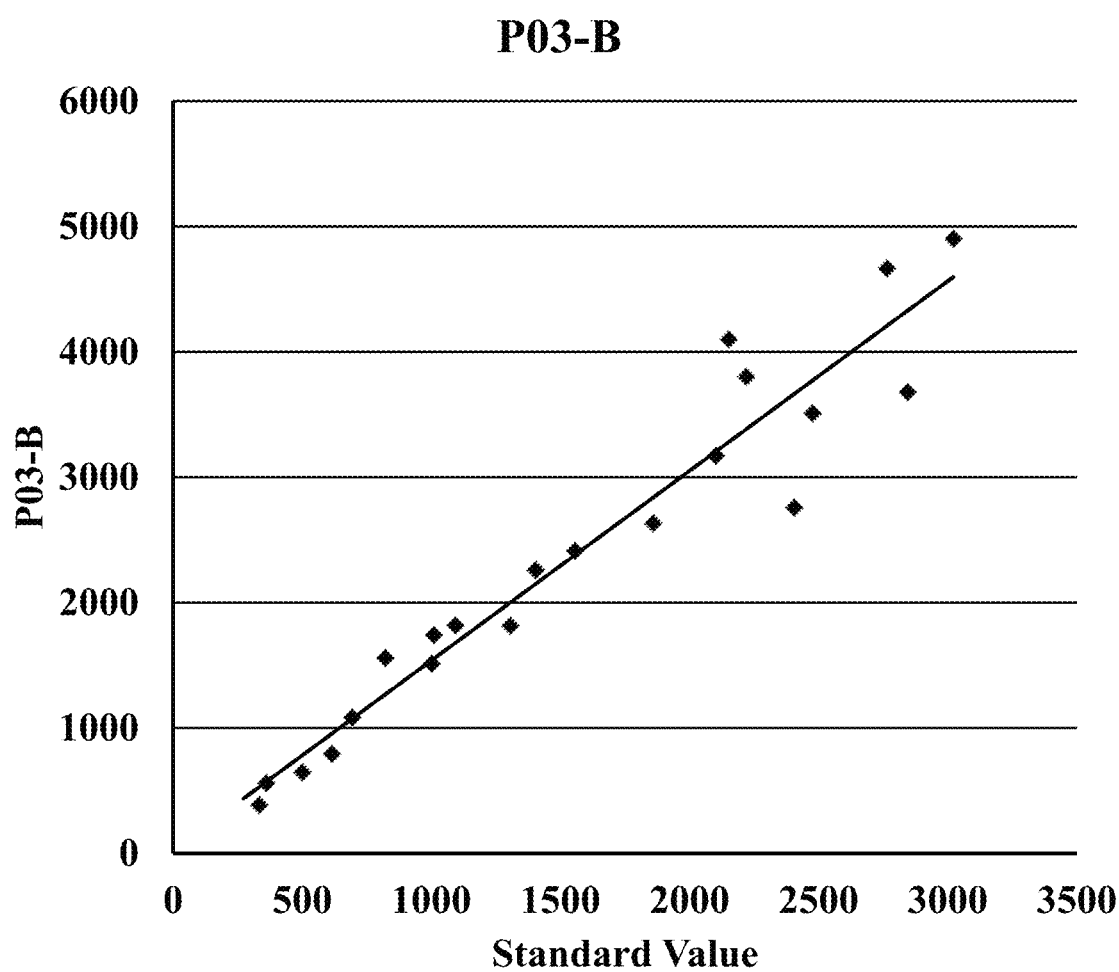

[Figure 3]
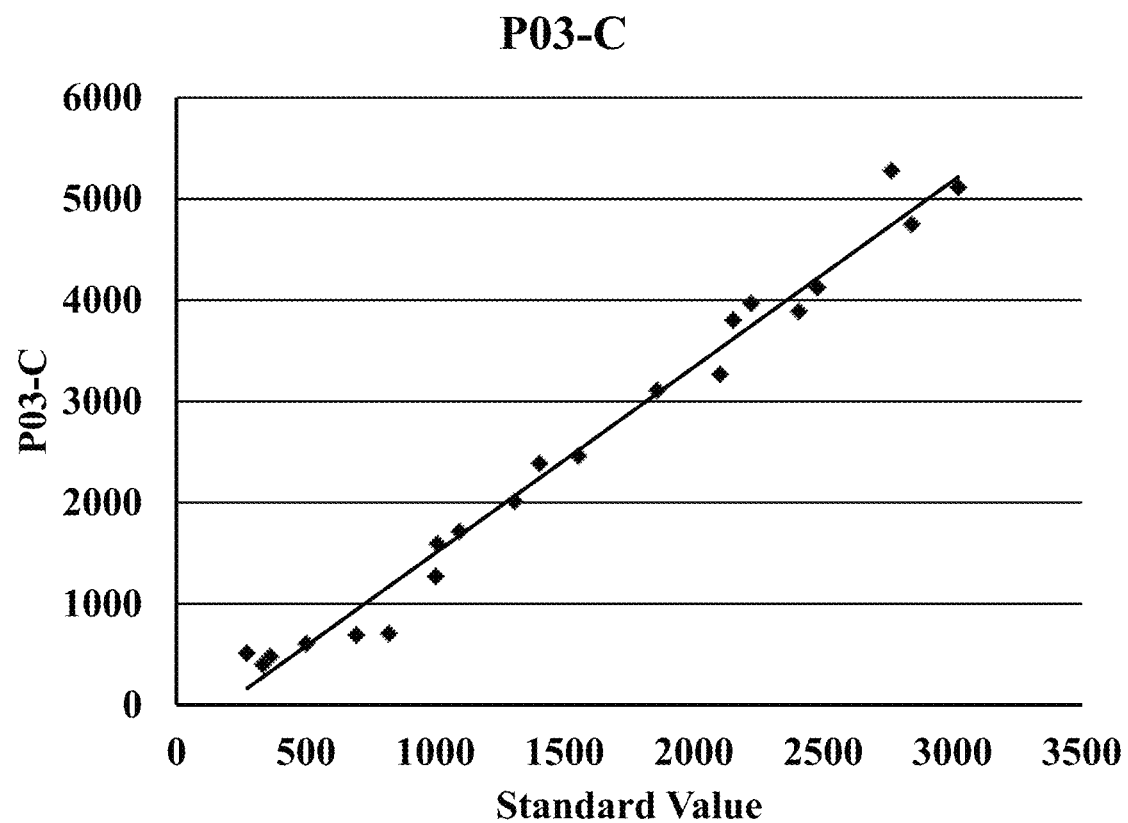

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial sequence
<220> FEATURE:
<223> OTHER INFORMATION: Synthetic Construct

<400> SEQUENCE: 1

Lys Arg Val Asp Ala Asp Ala Asp Pro Arg
1               5                   10

<210> SEQ ID NO 2
<211> LENGTH: 16
<212> TYPE: PRT
<213> ORGANISM: Artificial sequence
<220> FEATURE:
<223> OTHER INFORMATION: Synthetic Construct

<400> SEQUENCE: 2

Arg Val Asp Ala Asp Ala Asp Pro Arg Gln Tyr Ala Asp Thr Val Lys
1               5                   10                  15

<210> SEQ ID NO 3
<211> LENGTH: 356
```

<212> TYPE: PRT
<213> ORGANISM: Artificial sequence
<220> FEATURE:
<223> OTHER INFORMATION: Synthetic Construct

<400> SEQUENCE: 3

```
Thr Thr Pro Glu Pro Cys Glu Leu Asp Asp Glu Asp Phe Arg Cys Val
1               5                   10                  15

Cys Asn Phe Ser Glu Pro Gln Pro Asp Trp Ser Glu Ala Phe Gln Cys
            20                  25                  30

Val Ser Ala Val Glu Val Glu Ile His Ala Gly Gly Leu Asn Leu Glu
        35                  40                  45

Pro Phe Leu Lys Arg Val Asp Ala Asp Ala Asp Pro Arg Gln Tyr Ala
    50                  55                  60

Asp Thr Val Lys Ala Leu Arg Val Arg Arg Leu Thr Val Gly Ala Ala
65                  70                  75                  80

Gln Val Pro Ala Gln Leu Leu Val Gly Ala Leu Arg Val Leu Ala Tyr
                85                  90                  95

Ser Arg Leu Lys Glu Leu Thr Leu Glu Asp Leu Lys Ile Thr Gly Thr
            100                 105                 110

Met Pro Pro Leu Pro Leu Glu Ala Thr Gly Leu Ala Leu Ser Ser Leu
        115                 120                 125

Arg Leu Arg Asn Val Ser Trp Ala Thr Gly Arg Ser Trp Leu Ala Glu
    130                 135                 140

Leu Gln Gln Trp Leu Lys Pro Gly Leu Lys Val Leu Ser Ile Ala Gln
145                 150                 155                 160

Ala His Ser Pro Ala Phe Ser Cys Glu Gln Val Arg Ala Phe Pro Ala
                165                 170                 175

Leu Thr Ser Leu Asp Leu Ser Asp Asn Pro Gly Leu Gly Glu Arg Gly
            180                 185                 190

Leu Met Ala Ala Leu Cys Pro His Lys Phe Pro Ala Ile Gln Asn Leu
        195                 200                 205

Ala Leu Arg Asn Thr Gly Ile Glu Thr Pro Thr Gly Val Cys Ala Ala
    210                 215                 220

Leu Ala Ala Ala Gly Val Gln Pro His Ser Leu Asp Leu Ser His Asn
225                 230                 235                 240

Ser Leu Arg Ala Thr Val Asn Pro Ser Ala Pro Arg Cys Met Trp Ser
                245                 250                 255

Ser Ala Leu Asn Ser Leu Asn Leu Ser Phe Ala Gly Leu Glu Gln Val
            260                 265                 270

Pro Lys Gly Leu Pro Ala Lys Leu Arg Val Leu Asp Leu Ser Cys Asn
        275                 280                 285

Arg Leu Asn Arg Ala Pro Gln Pro Asp Glu Leu Pro Glu Val Asp Asn
    290                 295                 300

Leu Thr Leu Asp Gly Asn Pro Phe Leu Val Pro Gly Thr Ala Leu Pro
305                 310                 315                 320

His Glu Gly Ser Met Asn Ser Gly Val Val Pro Ala Cys Ala Arg Ser
                325                 330                 335

Thr Leu Ser Val Gly Val Ser Gly Thr Leu Val Leu Leu Gln Gly Ala
            340                 345                 350

Arg Gly Phe Ala
            355
```

<210> SEQ ID NO 4
<211> LENGTH: 11

```
<212> TYPE: PRT
<213> ORGANISM: Artificial sequence
<220> FEATURE:
<223> OTHER INFORMATION: Synthetic Construct

<400> SEQUENCE: 4

Cys Lys Arg Val Asp Ala Asp Ala Asp Pro Arg
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic Construct

<400> SEQUENCE: 5

Lys Arg Val Asp Ala Asp Ala Asp Pro Arg Cys
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic Construct

<400> SEQUENCE: 6

Asn Leu Glu Pro Phe Leu Lys Arg Val Asp
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic Construct

<400> SEQUENCE: 7

Pro Phe Leu Lys Arg Val Asp Ala Asp Ala
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic Construct

<400> SEQUENCE: 8

Asp Ala Asp Ala Asp Pro Arg Gln Tyr Ala
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic Construct

<400> SEQUENCE: 9

Ala Asp Pro Arg Gln Tyr Ala Asp Thr Val
1               5                   10

<210> SEQ ID NO 10
<211> LENGTH: 10
<212> TYPE: PRT
```

```
<213> ORGANISM: Artificial sequence
<220> FEATURE:
<223> OTHER INFORMATION: Synthetic Construct

<400> SEQUENCE: 10

Arg Gln Tyr Ala Asp Thr Val Lys Ala Leu
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic Construct

<400> SEQUENCE: 11

Ala Asp Thr Val Lys Ala Leu Arg Val Arg
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic Construct

<400> SEQUENCE: 12

Val Lys Ala Leu Arg Val Arg Arg Leu Thr
1               5                   10
```

SPECIFICALLY PURIFIED ANTI-PRESEPSIN ANTIBODY

CROSS-REFERENCE TO RELATED APPLICATIONS

This application is a National Stage application of PCT/JP2015/073839, filed Aug. 25, 2015.

TECHNICAL FIELD

The present invention relates to anti-presepsin polyclonal antibodies useful for presepsin measurement in a samples.

BACKGROUND ART

CD14 is a known glycoprotein expressed on the membrane surface of monocytic cells and functions as a receptor of LPS (lipopolysaccharide). There are 2 forms of CD14 molecules. One is the membrane bound-form of CD14 (mCD14) expressed on the cell surface. Another form is soluble CD14 (sCD14). sCD14s that have a molecular weight of about 55 kDa and about 49 kDa (hereinafter, referred to as the "high molecular weight sCD14") are known in the art and these sCD14s are reported to show a high level in the blood of a patient with many diseases such as sepsis, acquired immune deficiency syndrome (AIDS), acute respiratory distress syndrome (ARDS) and systemic lupus erythematosus (SLE). For that reason, these high molecular weight sCD14s are not considered as disease-specific markers. See Non-Patent Documents 1 and 2.

Meanwhile, it has been reported that there is a new molecular species of sCD14, sCD14-ST (soluble CD14 antigen subtype, also referred to as presepsin), whose blood concentration is characteristically increased in sepsis patients.

sCD14-ST (presepsin) is characterized by being migrated to 13±2 kDa of the molecular weight in SDS-PAGE under non-reducing conditions of all sCD14s, and it comprises the N-terminal region of CD14. sCD14-ST (presepsin) has an amino acid sequence in which the C-terminal region is largely deleted compared to the amino acid sequences of high molecular weight sCD14, and unlike the high molecular weight sCD14, sCD14-ST (presepsin) does not have LPS binding ability. In addition, presepsin shows different immunogenicity from that of the high molecular weight sCD14, and therefore the molecules can be distinguished using the antibody. The blood concentration of presepsin specifically increases in sepsis patients (see Patent Document 1). Moreover, it is reported that the blood concentration of presepsin shows a higher level in the blood of sepsis patients compared to patients with systemic inflammatory response syndrome (SIRS), which is difficult to discriminate from sepsis. Thus, presepsin is considered a specific diagnosis marker of sepsis (see Non-Patent Document 3).

A rabbit-derived polyclonal antibody (S68 antibody) and a rat-derived monoclonal antibody (F1146-17-2), which specifically recognized presepsin, have been disclosed (see Patent Documents 1 and 2).

Presently, a measurement system using rabbit-derived polyclonal antibodies as a specific antibody to presepsin is practically used in the measurement to presepsin, and measurement kits are on the market in Europe and Japan (PATHFAST™ Presepsin, Mitsubishi Chemical Medience Corporation).

Rabbit-derived polyclonal antibodies recognise various antigens and have strong affinity for antigen compared to antibodies derived from rodent such as a mouse. On the other hand, it is that the considerable individual variability of rabbits provides difficulty of producing antibody stability and these are thought to have greater lot-to-lot variation.

BACKGROUND ART DOCUMENT

Patent Document

Patent Document 1: WO2005/108429
Patent Document 2: WO 2004/044005

Non Patent Document

Non-Patent Document 1: Hayashi et al., Infection and Immunity, 67: 417-420, 1999
Non-Patent Document 2: Lawn et al., Clinical & Experimental Immunology, 120: 483-487, 2000
Non-Patent Document 3: Yaegashi et al., Journal of Infection and Chemotherapy, 11: 234-238, 2005

SUMMARY OF THE INVENTION

Problem to be Solved by the Invention

Presepsin has been conventionally measured by using the anti-presepsin polyclonal antibodies (S68 antibodies) derived from rabbits. However, it has been found that when samples are measured by constructing ELISA with S68 antibodies, there is a relatively large variation in measured values among different antibody lots.

A problem of the present invention is to provide anti-presepsin polyclonal antibodies which have less variation in measured values among antibody lots compared to S68 antibodies and thus are suitable for presepsin measurement.

Another problem of the present invention is to provide a highly specific antibody that specifically binds to presepsin and causes less cross-reaction with high molecular weight sCD14 in human blood.

Another problem of the present invention is to provide anti-presepsin polyclonal antibodies having higher reactivity with presepsin than S68 antibodies.

The purpose of the present invention is to provide anti-presepsin polyclonal antibodies which can solve at least one of the above problems.

Means for Solving the Problem

The conventional anti-presepsin polyclonal rabbit-derived antibodies (S68 antibodies) are prepared by purifying using S68 peptide-immobilized affinity column to polyclonal antibodies obtained by immunising rabbits with S68 peptide (SEQ ID NO: 2). The inventor of the present invention has found that highly reactivity polyclonal has been obtained by shifting the affinity column for purifying from S68 peptide-immobilized affinity column to P03 peptide (SEQ ID NO: 1)-immobilized affinity column, The P03 peptide has a sequence containing a part of S68 peptide.

The inventor of the present invention confirmed that the specificity of the polyclonal antibodies obtained via purification using P03 peptide by peptide competitive inhibition assay. The inventor has found that anti-presepsin polyclonal antibodies which specifically bind to P03 peptide (hereinafter also referred to as "P03-specific polyclonal antibodies") have properties to have less lot-to-lot of antibodies variation in measured values than S68 antibodies and cause less cross-reaction with high molecular weight soluble CD14 (hereinafter also referred to as "high molecular weight sCD14 in blood") in human blood, that are suitable for presepsin measurement, and therefore the inventor has completed the present invention.

Namely, with regard to the lot-to-lot variation of measured values, 3 lots of P03-specific polyclonal antibodies and 3 lots of S68 antibodies were used and those presepsin concentration were measured. Presepsin concentration of plurality of samples (in known concentration of presepsin) was also measured. Then correlation analysis was performed between the obtained measured values and the known concentration, and the coefficient of variance (CV) of the slopes of the regression lines was evaluated in Examples. The CV (10.6%) of the assay system of the P03-specific polyclonal antibodies was lower than that of S68 antibodies (20%), confirming that the assay system using the P03-specific polyclonal antibodies have the low lot-to-lot variation in measured values by examples.

With regard to the cross-reaction with high molecular weight sCD14 in blood, it was confirmed by the examples that the cross-reaction with high molecular weight sCD14 in blood was under the limit of detection in the ELISA assay system using the P03-specific polyclonal antibodies.

Specific purification of polyclonal antibodies during the production process thereof is generally carried out with administered antigens (S68 peptide in the present invention) and it is not generally envisaged that there is a peptide that is more suitable for specific purification other than the administered antigen. It is surprising that the antibodies which are more suitable for presepsin measurement than S68 antibodies are now obtained by specific purification using P03 peptide having a sequence containing a part of S68 peptide.

Thus, the present invention is described below.

[1] Anti-presepsin polyclonal antibodies, wherein antibodies specifically bind to a peptide consisting of an amino acid sequence of SEQ ID NO: 1.

[2] Anti-presepsin polyclonal antibodies wherein a percentage of containing the anti-presepsin polyclonal antibodies specifically binding to a peptide consisting of an amino acid sequence of SEQ ID NO: 1 is higher than a percentage of containing, in S68 antibodies, of anti-presepsin polyclonal antibodies specifically binding to the peptide comprising the amino acid sequence of SEQ ID NO: 1.

[2-1] Anti-presepsin polyclonal antibodies, wherein the percentage of containing, in the anti-presepsin polyclonal antibodies, of anti-presepsin polyclonal antibodies specifically binding to a peptide comprising an amino acid sequence of SEQ ID NO: 1 is 40% or more.

[3] The antibodies according to any one of [1] to [2-1],
wherein the binding between the antibodies and presepsin is competitive-inhibited by 30% or more in a competitive reaction system that the peptide consist of the amino acid sequence of SEQ ID NO: 1 is subjected to competitive reaction so that the binding between the antibodies and presepsin is inhibited, and
wherein the binding between the antibodies and presepsin is competitive-inhibited by less than 30% in a competitive reaction system that peptide comprising an amino acid sequence of SEQ ID NO: 9 is subjected to competitive reaction so that the binding between the antibodies and presepsin is inhibited.

[3-1] The antibodies according to any one of [1] to [3], wherein the antibodies have on or more characteristics selected form the following (A) to (C):
(A) in a competitive reaction system of a peptide comprising an amino acid sequence of SEQ ID NO: 6 so as to inhibit binding between the antibodies and presepsin, binding between the antibodies and presepsin is competitive-inhibited by less than 30%;
(B) in a competitive reaction system of a peptide comprising an amino acid sequence of SEQ ID NO: 7 so as to inhibit binding between the antibodies and presepsin, binding between the antibodies and presepsin is competitive-inhibited by less than 30%; and
(C) in a reaction competitive system of a peptide comprising an amino acid sequence of SEQ ID NO: 8 so as to inhibit binding between the antibodies and presepsin, binding between the antibodies and presepsin is competitive-inhibited by less than 30%.

[4] The antibodies according to any one of [1] to [3-1], wherein when the antibodies are used in an ELISA assay system, the ELISA assay system has a lower incidence of cross-reaction with high molecular weight soluble CD14 in human blood than an ELISA assay system using S68 antibodies.

[5] The antibodies according to any one of [1] to [4], wherein when the antibodies are used in an ELISA assay system to measure a presepsin concentration of samples (in known concentration of presepsin) containing presepsin in order to carry out correlation analysis of measured values and the known concentration, a coefficient of variance (CV) of slopes of regression lines is 15% or less.

[6] The antibodies according to any one of [1] to [5], wherein the antibody bind to presepsin at an affinity (KD) of less than $10^{-7}$.

[7] The antibodies according to any one of [1] to [6], wherein the antibodies are obtained by purifying polyclonal antibodies obtained from a non-human mammal immunised by a peptide, as an immunogen, including amino acid residues from position 1 to position 9 of an amino acid sequence of SEQ ID NO: 2 and including 9 or more consecutive amino acid residues in the amino acid sequence of SEQ ID NO: 2.

[8] The antibodies according to any one of [1] to [6], obtained by subjecting polyclonal antibodies by a treatment to increase a proportion of antibodies specifically binding to the peptide comprising the amino acid sequence of SEQ ID NO: 1, wherein the polyclonal antibodies are obtained from a non-human mammal immunised by a peptide, as an immunogen, including amino acid residues from position 1 to position 9 of an amino acid sequence of SEQ ID NO: 2 and including 9 or more consecutive amino acid residues in the amino acid sequence of SEQ ID NO: 2.

[9] Anti-presepsin polyclonal antibodies obtained by purifying, using a column to which a peptide comprising an amino acid sequence of SEQ ID NO: 1 is immobilised, polyclonal antibodies obtained from a non-human mammal immunised using, as an immunogen, a peptide including amino acid residues from positions 1 to 9 of an amino acid sequence of SEQ ID NO: 2 and including 9 or more consecutive amino acid residues in the amino acid sequence of SEQ ID NO: 2.

[10] The antibodies according to [9], further subjected to a treatment that eliminates antibodies binding to a peptide comprising an amino acid sequence of SEQ ID NO: 8.

[11] The antibodies according to [9], further subjected to a treatment that reduces a binding activity of antibodies binding to a peptide comprising an amino acid sequence of SEQ ID NO: 8.

[11-1] The antibodies according to any one of [9] to [11], wherein the binding between the antibodies and presepsin is competitive-inhibited by 30% or more in a competitive reaction system of the peptide comprising the amino acid sequence of SEQ ID NO: 1 so as to inhibit binding between the antibodies and presepsin, and the binding between the antibodies and presepsin is competitive-inhibited by 30% or less in a competitive reaction system of a peptide comprising an amino acid sequence of SEQ ID NO: 9 so as to inhibit binding between the antibodies and presepsin.

[11-2] The antibodies according to any one of [9] to [11-1], wherein when the antibodies are used in an ELISA assay system, the ELISA assay system has a lower incidence of cross-reaction with high molecular weight soluble CD14 in human blood than an ELISA assay system using S68 antibodies.

[11-3] The antibodies according to any one of [9] to [11-2], wherein when the antibodies are used in an ELISA assay system to measure a presepsin concentration of samples (in known concentration of presepsin) containing presepsin in order to carry out correlation analysis of measured values and the known concentration, a coefficient of variance (CV) of slopes of regression lines is 15% or less.

[11-4] The antibodies according to any one of [9] to [11-3], binding to presepsin at an affinity (KD) of less than $10^{-7}$.

[12] A method for producing anti-presepsin polyclonal antibodies, comprising at least the following steps; the step of obtaining polyclonal antibodies from a non-human mammal immunised using a peptide, as an immunogen, including amino acid residues from position 1 to position 9 of an amino acid sequence of SEQ ID NO: 2 and including 9 or more consecutive amino acid residues in the amino acid sequence of SEQ ID NO: 2; and the step of purifying the obtained antibodies using a column to which a peptide comprising an amino acid sequence of SEQ ID NO: 1 is immobilised.

[13] The method for producing anti-presepsin polyclonal antibodies according to [12], further comprising the step of eliminating antibodies binding to a peptide comprising an amino acid sequence of SEQ ID NO: 8.

[14] A method for measuring presepsin, comprising at least the step of exposing the antibodies according to any one of [1] to [11-4] to a sample containing presepsin.

[15] A kit for measuring presepsin, comprising at least the antibodies according to any one of [1] to [11-4].

[16] A kit for detecting sepsis or a kit for assisting detection or diagnosis of sepsis, comprising at least the antibodies according to any one of [1] to [11-4].

Effect of the Invention

The present invention provides anti-presepsin polyclonal antibodies having excellent reactivity with presepsin and being suitable for presepsin measurement of samples. Accordingly, it is possible to increase the quality and accuracy of presepsin measurement.

In one preferable embodiment, the antibody of the present invention have less lot-to-lot variation of antibodies in measured values during presepsin measurement using the antibodies and therefore it is possible to stably provide antibody having constant quality and excellent in practicality for suitable for presepsin measurement.

It is generally important that in measurement of samples using antibodies (particularly in diagnostic drugs), slopes of regression lines as shown in Example 5 fall within a certain range even among different lots of antibody. In one preferable embodiment, the antibodies of the present invention have a CV of slopes of regression lines of about 10% and thus slopes of regression lines tend to fall within a standard even among different lots of antibody.

In one further preferable embodiment, the antibodies of the present invention specifically bind to presepsin in a sandwich ELISA system and cause less cross-reaction with high molecular weight sCD14 in human blood compared to S68 antibodies, and thus allow measurement with high specificity.

BRIEF DESCRIPTION OF DRAWINGS

FIG. 1 shows a regression line of P03-specific polyclonal antibodies (P03-A) obtained in Example 5.

FIG. 2 shows a regression line of P03-specific polyclonal antibodies (P03-B) obtained in Example 5.

FIG. 3 shows a regression line of P03-specific polyclonal antibodies (P03-C) obtained in Example 5.

EMBODIMENTS FOR CARRYING OUT OF THE INVENTION

Hereinafter, the present invention will be described in more detail. The following embodiments are examples in order to describe the present invention and it is not intended to limit the present invention to the embodiments. It is to be understood that methods and compositions described herein are not limited to the particular embodiments described, and as such may vary.

1. Antibodies of the Present Invention

The present invention provides following anti-presepsin polyclonal antibodies (hereinafter referred to as "antibodies of the present invention"):

(1) anti-presepsin polyclonal antibodies (P03-specific polyclonal antibodies) specifically binding to a peptide comprising an amino acid sequence of SEQ ID NO: 1; or (2) anti-presepsin polyclonal antibodies whose percentage of containing the anti-presepsin polyclonal antibodies (P03-specific polyclonal antibodies) specifically binding to a peptide comprising an amino acid sequence of SEQ ID NO: 1 is higher than a percentage of containing anti-presepsin polyclonal antibody (P03-specific polyclonal antibody) specifically binding to a peptide comprising an amino acid sequence of SEQ ID NO: 1 in S68 antibody.

The "presepsin" is also called as sCD14-ST (soluble CD14 antigen subtype). As described above, there are two forms of CD14 which are membrane-bound CD14 (mCD14) and soluble CD14 (sCD14), and there is a plurality of soluble CD14s having different molecular weights in blood. Presepsin is a fragment of a soluble CD14 and is a substance having characteristics as shown in 1) to 3) below:

1) it has a molecular weight of 13±2 kDa according to SDS-PAGE under non-reducing conditions;

2) it has an amino acid sequence of position 1 to position 11 of the amino acid sequence (full-length amino acid sequence of human soluble CD14) of SEQ ID NO: 3 at the N-terminal; and 3) it specifically binds to an antibody prepared by using a peptide (S68 peptide) consisting of 16 amino acid residues (corresponding to the amino acid sequence from positions 53 to 68 in the amino acid sequence of SEQ ID NO: 3) described in SEQ ID NO: 2 for antigen.

In the present invention, presepsin means human presepsin unless particularly illustrated otherwise. For example, presepsin is a standard presepsin (rsCD14-ST disclosed in Example 16 of WO2005/108429). Alternatively, a substance having a binding activity as presepsin and partially modified from presepsin is used.

As described herein, "anti-presepsin polyclonal antibodies" mean polyclonal antibodies which immunologically recognise presepsin and/or polyclonal antibodies which have normal antigen-antibody reaction with presepsin. The antigen-antibody reaction may be verified by agglutination methods, sandwich methods, direct solid phase methods, competitive methods and so on. Expressing binding between antibodies and subject recognised by antibodies as an affinity, an equilibrium dissociation constant (KD) is generally less than $10^{-7}$ M.

As described herein, "peptide comprising an amino acid sequence of SEQ ID NO: 1" means P03 peptide. As used herein, "P03 peptide" means a peptide comprising an amino acid sequence corresponding to position 52 to position 61 of human full-length soluble CD14 (SEQ ID NO: 3).

The term "specifically binding to a peptide comprising an amino acid sequence of SEQ ID NO: 1" means that antibodies specifically bind to the amino acid sequence of SEQ ID NO: 1 (P03 peptide), but do not bind to other peptides in the amino acid sequence of presepsin. In other words, antibodies specifically recognise an epitope in the amino acid sequence of P03 peptide, but do not recognise other peptides. In further detail, for example, according to the description in Example 3 in the present invention, the term may be represented by that when a peptide competitive inhibition assay (preferably using absorbance) is carried out, the competitive inhibition of binding between antibodies of the present invention and presepsin is 30% or more by addition of P03 peptide and is less than 30% by addition of other peptides.

As described herein, "other peptides" is, for example, a peptide comprising an amino acid sequence of SEQ ID NO: 6 (P01 peptide), a peptide comprising an amino acid sequence of SEQ ID NO: 7 (P02 peptide), a peptide comprising an amino acid sequence of SEQ ID NO: 8 (P04 peptide), a peptide comprising an amino acid sequence of SEQ ID NO: 9 (P05 peptide), a peptide comprising an amino acid sequence of SEQ ID NO: 10 (P06 peptide), a peptide comprising an amino acid sequence of SEQ ID NO: 11 (P07 peptide) and a peptide comprising an amino acid sequence of SEQ ID NO: 12 (P08 peptide). "Specific binding to a peptide comprising an amino acid sequence of SEQ ID NO: 1" includes specific binding to P03 peptide immobilised to a column. The "P03 peptide immobilised to a column" may include P03 peptide having cysteine linked at the N- or C-terminal and therefor bound to the column through the cysteine.

Herein the amino acid sequence of SEQ ID NO: 6 (P01 peptide) corresponds to the amino acid sequence from position 46 to position 55 of the amino acid sequence of SEQ ID NO: 3. The amino acid sequence of SEQ ID NO: 7 (P02 peptide) corresponds to the amino acid sequence from position 49 to position 58 of the amino acid sequence of SEQ ID NO: 3. The amino acid sequence of SEQ ID NO: 8 (P04 peptide) corresponds to the amino acid sequence from position 55 to position 64 of the amino acid sequence of SEQ ID NO: 3. The amino acid sequence of SEQ ID NO: 9 (P05 peptide) corresponds to the amino acid sequence from position 58 to position 67 of the amino acid sequence of SEQ ID NO: 3. The amino acid sequence of SEQ ID NO: 10 (P06 peptide) corresponds to the amino acid sequence from position 61 to position 70 of the amino acid sequence of SEQ ID NO: 3. The amino acid sequence of SEQ ID NO: 11 (P07 peptide) corresponds to the amino acid sequence from positions 64 to position 73 of the amino acid sequence of SEQ ID NO: 3. The amino acid sequence of SEQ ID NO: 12 (P08 peptide) corresponds to the amino acid sequence from position 67 to position 76 of the amino acid sequence of SEQ ID NO: 3.

As described herein, "a higher percentage of content, in the anti-presepsin polyclonal antibodies, of anti-presepsin polyclonal antibodies specifically binding to a peptide comprising an amino acid sequence of SEQ ID NO: 1 than a percentage of content, in S68 antibodies, of anti-presepsin polyclonal antibodies specifically binding to the peptide comprising the amino acid sequence of SEQ ID NO: 1" means that the proportion of P03-specific polyclonal antibodies in the anti-presepsin polyclonal antibodies is higher than the proportion of the P03-specific polyclonal antibodies in S68 antibodies. Such antibodies have a higher percentage of content of P03-specific polyclonal antibodies having preferable properties than that of S68 antibodies, and thus exhibit superior abilities compared to S68 antibodies.

Such antibodies can be obtained from, for example, polyclonal antibodies obtained from a non-human mammal immunised using a peptide, as an immunogen, including amino acid residues from position 1 to position 9 of an amino acid sequence of SEQ ID NO: 2 and including 9 or more consecutive amino acid residues in the amino acid sequence of SEQ ID NO: 2 by a treatment to increase a proportion of antibodies specifically binding to a peptide (P03 peptide) comprising an amino acid sequence of SEQ ID NO: 1. The details are described hereinafter.

The "S68 antibodies" mean anti-S68 peptide polyclonal antibodies obtained by purifying polyclonal antibodies obtained from a non-human mammal immunised with S68 peptide as an immunogen, using a S68 peptide immobilised column. The "S68 peptide" means a peptide consist of an amino acid sequence of SEQ ID NO: 2 (amino acid sequence from position 53 to position 68 in the amino acid sequence of SEQ ID NO: 3). A method in detail for preparing S68 antibodies is disclosed in Example 1 of WO2004/044005 and described in Example 1 herein below.

The calculation of the percentage of content of P03 specific polyclonal in anti-presepsin polyclonal antibodies and S68 antibodies may be made, for example, as described in Example 1 and Example 6, by purifying anti-presepsin polyclonal antibodies or S68 antibodies (A), and then obtaining P03-specific polyclonal antibodies (B), after that measuring the amount of protein for (A) and (B), and determining the ratio of (B) relative to (A), but is not particularly limited. The amount of protein is measured by using, for example, a method described in Example 1-3.

The percentages of content of P03-specific polyclonal antibodies in anti-presepsin polyclonal antibodies and in S68 antibodies are preferably compared as follows: the percentages of content are calculated for more than one lot of the respective anti-presepsin polyclonal antibodies and S68 antibodies and the averages of the percentages of content are compared. 3 lots or more are preferable, although it is not limited thereto.

Some of the preferable embodiments of the present invention are anti-presepsin polyclonal antibodies having a high percentage of content of anti-presepsin polyclonal antibodies (P03-specific polyclonal antibodies) specifically binding to a peptide comprising an amino acid sequence of SEQ ID NO: 1 in the anti-presepsin polyclonal antibodies.

The phrase "having a high percentage of content of P03-specific polyclonal antibodies in the anti-presepsin polyclonal antibodies" means that the proportion of P03-specific polyclonal antibodies in anti-presepsin polyclonal antibodies is preferably 40% or more, more preferably 50% or more, even more preferably 60% or more and particularly preferably 70% or more. The percentage of content of P03-specific polyclonal antibodies in polyclonal antibodies may be calculated as described above.

In the embodiment, antibodies included in the anti-presepsin polyclonal antibodies is the P03-specific polyclonal antibodies, and in addition (1) anti-presepsin polyclonal antibodies which recognise P03 peptide and recognise other peptides, and (2) anti-presepsin polyclonal antibodies which do not recognise P03 peptide but recognise other peptides. The "other peptides" is, for example, P01 peptide, P02 peptide, P04 peptide, P05 peptide, P06 peptide, P07 peptide and P08 peptide.

Such antibodies may be obtained by, for example, subjecting polyclonal antibodies obtained from a non-human mammal immunised using a peptide, as an immunogen, including amino acid residues from position 1 to position 9 of an amino acid sequence of SEQ ID NO: 2 and including 9 or more consecutive amino acid residues in the amino acid sequence of SEQ ID NO: 2 to a treatment to increase the proportion of antibodies specifically binding to a peptide (P03 peptide) comprising an amino acid sequence of SEQ ID NO: 1. The details are described hereinafter.

As used herein, the term "antibody" means "an antibody or an antigen binding fragment thereof" unless particularly illustrated otherwise. The term "antigen binding fragment" means a fragment having the substantially same antigen-binding property as the original antibody in the partial fragment of antibody. Examples of the antigen binding fragment include Fab, Fab', F(ab')$_2$ and the like.

The antibodies of the present invention are derived from non-human mammals. The antibodies of the present invention are derived from non-human mammals is, for example, a rabbit, a goat, a horse, a sheep, a pig, a rat, a mouse and the like. Because of an ease of antibody preparation, it is preferably a rabbit, a goat and the like and it is more preferably a rabbit.

The antibodies of the present invention have excellent reactivity with presepsin and are suitable for presepsin measurement in samples. The reactivity of the antibodies of the present invention with presepsin may be evaluated by a sandwich ELISA system constructed by the antibodies of the present invention. The sandwich ELISA system is preferably one using (a) the antibodies of the present invention and (b) F1106-13-3 antibody or F1031-8-3 antibody (disclosed in Example 3 of WO2004/044005). In more detail, according to the description in Example 2, the reactivity of the antibodies of the present invention with presepsin may be evaluated by absorbance when the antibodies of the present invention immobilised to a solid phase react with presepsin. As described in Example 2, the ratio (S/N ratio) of the absorbance of the antibodies which react with 500 pg/mL of presepsin relative to the absorbance obtained when the antibodies are allowed to react with 0 pg/mL of presepsin which is regarded as 1 may be used for evaluation of the reactivity with presepsin. An S/N ration of the antibodies of the present invention is preferably 36 or more, more preferably 40 or more and even more preferably 45 or more. An S/N ration of the antibodies of the present invention is higher than that of S68 antibodies, and is preferably 1.2 times or more, more preferably 2 times or more and even more preferably 2 to 3 times higher than that of S68 antibodies.

The antibodies of the present invention specifically bind to presepsin and have preferably a better affinity to presepsin than S68 antibodies have. The antibodies of the present invention preferably have an affinity to presepsin (the dissociation equilibrium constant, KD) of less than $10^{-7}$ M and more preferably less than $10^{-8}$M. The dissociation equilibrium constant of the antibodies of the present invention to presepsin is, for example, in the range of $10^{-7}$ M to $10^{-13}$ M.

The affinity (the dissociation equilibrium constant, KD) can be measured with, for example, BIAcore (GE Healthcare).

Preferably, the antibodies of the present invention may be characterised by competitive-inhibition of 30% or more for the binding between the antibodies and presepsin according to a reaction system (preferably using absorbance) in which P03 peptide is used for competitive reaction to inhibit the binding between the antibodies and presepsin, and competitive-inhibition of 30% or less for the binding between the antibodies and presepsin according to a reaction system (preferably using absorbance) in which P05 peptide used for competitive reaction to inhibit the binding between antibodies and presepsin. Preferably, the reaction system is sandwich ELISA. More preferably, the reaction system is sandwich ELISA in which (a) the antibodies of the present invention and (b) F1106-13-3 antibody or F1031-8-3 antibody (disclosed in Example 3 of WO2004/044005) are used. In more detail, the competitive inhibition reaction may be evaluated by the method described in Example 3.

More preferably, the antibodies of the present invention may be characterized by competitive-inhibited of less than 30% by P01 peptide, P06 peptide, P07 peptide and P08 peptide. Even more preferably, the antibodies of the present invention may be characterized by competitive-inhibited by less than 30% by at least one peptide selected from P02 peptide and P04 peptide. Most preferably, the antibodies of the present invention may be characterized by competitive-inhibited by less than 30% by P02 peptide and P04 peptide.

Preferably, the antibodies of the present invention specifically bind to presepsin and have low incidence of cross-reaction with soluble CD14 of about 55 kDa and about 49 kDa (hereinafter also referred to as "high molecular weight sCD14 in blood") which are major soluble CD14 in human blood. Presepsin has a different molecular weight from high molecular weight sCD14 and has a shorter amino acid sequence than high molecular weight sCD14. Because of the reasons described above, presepsin has a different structure from high molecular weight sCD14 in blood and the antibody has different reactivities to the molecules so that it is considered that the antibodies of the present invention more strongly bind to presepsin.

The cross reaction may be evaluated by constructing a sandwich ELISA system using the antibodies of the present invention. The sandwich ELISA system is more preferably one in which (a) the antibodies of the present invention and (b) F1106-13-3 antibody or F1031-8-3 antibody (disclosed in Example 3 of WO2004/044005) are used. In more detail, the cross reaction may be evaluated by the method described in Example 4. According to Example 4, the cross reaction with the antibodies of the present invention may be evaluated by absorbance when the antibodies of the present invention immobilised to a solid phase react with high molecular weight sCD14 in serum.

As for the high molecular weight sCD14, the human full-length soluble CD14 comprising the amino acid sequence described in SEQ ID NO: 3 may be used or it may be prepared by affinity column adsorption using 3C10 antibody of body fluid of normal human subjects, for example (see Example 23 in WO2005/108429). Samples containing high molecular weight sCD14 in blood may be prepared by using normal human serum and CD14 absorbed human serum (serum containing decreased amount of high molecular weight sCD14 in blood), for example. CD14 absorbed human serum may be obtained according to the description in Example 4, by applying normal human serum to an immobilised-anti-CD14 antibody affinity column, for example.

The cross reaction may be calculated, for example, according to the following equation.

Cross reaction (%)=(Concentration determined by plotting the absorbance of a sample containing high molecular weight sCD14 in blood measured with the antibodies on a presepsin standard curve/Concentration of high molecular weight sCD14 used for the measurement)×100

The cross reaction of the antibodies of the present invention to high molecular weight sCD14 as determined according to the above equation is preferably at or under the limit of detection.

Preferably, an ELISA assay system using antibodies of the present invention may have a lower incidence of cross-reaction (has lower cross reaction (%)) with high molecular weight sCD14 in blood than an ELISA assay system using S68 antibodies. When comparing incidences of cross-reaction, it is preferable to compare averages of the cross reaction of more than one lot (for example, 3 lots or more) of antibodies.

The antibodies of the present invention are characterised in that when the antibodies are used for presepsin measurement of human serum, a variation in measured values between lot-to-lot differences of antibodies is lower compared to S68 antibodies and the antibodies have high uniformity of the lot-to-lot of antibody. Presepsin concentration in human serum may be measured in order to evaluate the variation of measured values of the lot-to-lot by constructing a sandwich ELISA system using the antibodies of the present invention. The sandwich ELISA system is more preferably one in which (a) the antibodies of the present invention and (b) F1106-13-3 antibody or F1031-8-3 antibody (disclosed in Example 3 of WO2004/044005) are used.

In more detail, the variation of measured values of the lot-to-lot may be evaluated, according to the method described in Example 5. According to the description in Example 5, the antibodies of the present invention (for example, 3 lots are used) are immobilised to a solid phase, the presepsin concentration of more than one samples (in known concentration of presepsin) is measured, and correlation analysis with the obtained measured values and known concentration is carried out to determine regression lines and the coefficient of variance (CV) of the slopes of the regression lines may be determined. The CV of the determined slopes may be used for evaluation of the variation of measured values of the lot-to-lot of the antibodies. The CV of the slope of the antibodies according to a preferable embodiment of the present invention is preferably 15% or less, more preferably 13% or less and particularly preferably 11% or less. In another preferred embodiment, the CV of the slopes of the antibodies of the present invention is smaller than that of S68 antibodies, and the difference of the slope is preferably 3% or more, more preferably 5% or more and even more preferably 8% or more. To measure the standard samples in known concentration of presepsin is preferable to use a presepsin measurement kit using S68 antibodies (such as PATHFAST™ Presepsin, Mitsubishi Chemical Medience Corporation).

As for the antibodies of the present invention, when a measurement system is constructed and presepsin is measured in more than one sample (in known concentration of presepsin), the antibodies are preferable to have a good correlation between measured values and known concentrations. Having a good correlation means a correlation coefficient of preferably 0.9 or more and more preferably 0.95 or more.

In some embodiments of the present invention, the antibodies of the present invention are purified.

The antibodies of the present invention may be obtained by, for example, purifying polyclonal antibodies obtained from a non-human mammal immunised using a peptide (for example, S68 peptide), as an immunogen, including amino acid residues from position 1 to position 9 of an amino acid sequence of SEQ ID NO: 2 and including 9 or more consecutive amino acid residues in the amino acid sequence of SEQ ID NO: 2.

Alternatively, the antibodies of the present invention may be obtained by subjecting polyclonal antibodies to a treatment to increase a proportion of antibodies specifically binding to a peptide (P03 peptide) comprising an amino acid sequence of SEQ ID NO: 1, the polyclonal antibodies being obtained from a rabbit immunised using a peptide (for example, S68 peptide), as an immunogen, including amino acid residues from position 1 to position 9 of an amino acid sequence of SEQ ID NO: 2 and including 9 or more consecutive amino acid residues in the amino acid sequence of SEQ ID NO: 2.

A specific method for producing the antibodies of the present invention is described hereinbelow.

2. Method for Producing Antibodies of the Present Invention

The present invention provides a method for producing the anti-presepsin polyclonal antibodies, comprising the step of: obtaining polyclonal antibodies from a non-human mammal immunised using a peptide, as an immunogen, including amino acid residues from position 1 to position 9 of an amino acid sequence of SEQ ID NO: 2 and including 9 or more consecutive amino acid residues in the amino acid sequence of SEQ ID NO: 2; and the step of purifying the obtained antibodies using a column with immobilised peptide (P03 peptide) comprising an amino acid sequence of SEQ ID NO: 1.

In the production of the antibodies of the present invention, the peptide used as an immunogen includes amino acid residues from position 1 to position 9 of the amino acid sequence of SEQ ID NO: 2 and includes 9 or more consecutive amino acid residues in the amino acid sequence of SEQ ID NO: 2. The term "9 or more consecutive amino acid residues" is preferably 10 or more consecutive, more preferably 12 or more consecutive, particularly preferably 16 consecutive amino acid residues. In addition, the peptide used as an antigen is not limited, in terms of other parts of the amino acid sequence, as far as the peptide includes 9 or more consecutive amino acids in amino acid residues indicated in SEQ ID NO: 2, but the peptide is preferable to have an amino acid sequence whole of which derives from the amino acid sequence of SEQ ID NO: 2. Cysteine may be inserted at the N- or C-terminal (preferably N-terminal) of the peptide in order to allow binding of a carrier described hereinbelow through an SH group. The peptide used as an immunogen is particularly preferably a peptide (S68 peptide) consisting of 16 consecutive amino acid residues (namely, all amino acid residues) in the amino acid sequence of SEQ ID NO: 2, and may have cysteine inserted at the N- or C-terminal (preferably N-terminal) thereof.

A method for preparing a peptide used as an immunogen may be a method using a generally used peptide synthesiser (peptide synthesiser 433A, PerkinElmer Japan Co., Ltd.) and the like, a gene recombination method (Division of Cancer Research, The Institute of Medical Science, The University of Tokyo Ed., *Shin Saibo Kogaku Jikken Protcol* (New Protocols of Cellular Engineering Experiments), Shujunsha Co., Ltd.) and the like.

For example, a peptide including 9 or more consecutive amino acid residues in the amino acid sequence of SEQ ID NO: 2 may be synthesised on 433A peptide synthesiser by Fmoc method, and after deprotection using TFA and cleavage from the resin, the peptide may be purified by using a C18 HPLC column (Capcell-pak, Shiseido Company, Limited) and a desired peptide may be prepared.

When an antigen is a protein, the protein may be used as an immunogen directly. However, when a peptide includes 8 to 30 amino acid residues or less, the peptide may generally not have immunogenicity because of the low molecular weight. In this case, the peptide may be linked to a carrier or the peptide may be used to prepare a MAP peptide by the multiple antigen peptide (MAP) method in order to impart the molecular weight which exhibits immunogenicity, so as to obtain the immunogen.

As for the carrier linked to the peptide described above may be a carrier protein or a polymer. The carrier protein which may be used is a heterogeneous protein such as bovine serum albumin, keyhole-limpet hemocyanin (KLH), thyroglobulin and ovalbumin. These carrier proteins may be linked to the peptide by utilising a side-chain functional group in an amino acid of the peptide or the carrier protein, or may be linked by introducing a maleimide group, an N-hydroxysuccinimide (NHS) group or an aldehyde group. In this case, an amino acid (for example, cysteine) of which functional group may be utilised may be linked to the peptide. The polymer may be saccharides such as mannan or chitosan and the like, or polyvinylpyrrolidone (PVA). These polymers may be linked to the peptide by adsorption or chemical bonding as described above.

In some embodiments of the present invention, the immunogen is S68 peptide linked to KLH (S68peptide-KLH) through cysteine inserted at the N-terminal.

By using the immunogen prepared as above, the polyclonal antibodies directed to the immunogen may be prepared according to a well-known technique (for example, see *Men-eki Jikken Sosaho* (Immunological Experimental Procedures), Japanese Society for Immunology Ed., published by Japanese Society for Immunology).

A non-human mammal is immunised with the immunogen prepared as above. For example, a non-human mammal is immunised with the 20 to 1000 µg of immunogen mixed with an adjuvant such as non-Freund's complete adjuvant, RIBI adjuvant, ALUM or the like. The non-human mammal is preferably a rabbit, a goat, a horse, a sheep, a pig, a rat, a mouse and the like, among which a rabbit or a goat is preferred and a rabbit is more preferred. Immunization may be carried out by intramuscular administration, intradermal administration, subcutaneous administration, intraperitoneal administration, lymph node administration and the like. Booster immunisation may be carried out by similarly administering the immunogen mixed with adjuvant such as incomplete Freund's adjuvant, RIBI adjuvant, ALUM or the like, or by directly administering the immunogen intravenously at an interval of 1 to 4 weeks after the initial administration.

The polyclonal antibodies directed to the immunogen may be collected from blood or peritoneal fluid, preferably from blood, of the non-human mammal immunised according to the above method. Blood is collected from the immunised non-human mammal according to a normal blood collecting method such as from the carotid artery, auricle vein, heart, leg vein and the like. From the collected blood, antiserum may be separated by centrifugation or the like. For preparation of polyclonal antibodies, it is preferable to use antiserum obtained from individuals of immunised non-human mammal having an antibody titre. The antibody titre in antiserum may be measured by, for example, allowing reaction of labelled P03 peptide with antiserum and then measuring the activity of the label bound to P03 peptide, or allowing reaction of P03 peptide immobilised on a plate with antiserum and detecting the amount of antibodies bound to P03 peptide using a labelled secondary antibody. The antiserum is then subjected to precipitation of a γ-globulin fraction by salting-out in which ammonium sulphate, sodium sulphate or the like is added and dialysis in an appropriate buffer, and polyclonal antibodies directed to the immunogen (for example, purified polyclonal antibodies of the IgG fraction) may then be prepared by using an affinity matrix that can specifically purify γ-globulin such as Protein A and Protein G.

The thus prepared polyclonal antibodies may contain, in addition to P03-specific polyclonal antibodies, anti-presepsin polyclonal antibodies other than P03-specific polyclonal antibodies. In the present invention, the thus prepared polyclonal antibodies are subjected to a treatment that increases the proportion of antibodies specifically binding to P03 peptide. The treatment may include, for example, purification.

In order to purify anti-presepsin polyclonal antibodies binding to P03 peptide (referred to as "P03 purified polyclonal antibodies") from the obtained polyclonal antibodies, purification is carried out by using an affinity matrix. In more detail, the affinity matrix is a column to which P03 peptide is immobilised. As P03 peptide binds to the column through an SH group, cysteine may be linked at the N- or C-terminal. The amino acid sequence of P03 peptide having cysteine linked at the N-terminal thereof and the amino acid sequence of P03 peptide having cysteine linked at the C-terminal thereof are indicated in SEQ ID NO: 4 and SEQ ID NO: 5, respectively. Preferably, the P03 peptide-immobilised column is a column to which both P03 peptide having cysteine linked at the N-terminal thereof and P03 peptide having cysteine linked at the C-terminal thereof are linked. P03 purified polyclonal antibodies may be prepared by purifying the purified IgG fraction obtained as above on such a column.

P03 purified polyclonal antibodies are antibodies obtained by purification using P03 peptide as above and binding to P03 peptide, and the percentage of content of P03-specific polyclonal antibodies in P03 purified polyclonal antibodies is higher than the percentage of content of P03-specific polyclonal antibodies in S68 antibodies. Therefore, P03 purified polyclonal antibodies can exhibit excellent properties derived from P03-specific polyclonal antibodies compared to S68 antibodies.

As needed, specificity of the obtained antibodies may be confirmed by carrying out a peptide competitive inhibition assay according to the description in Example 3 and, according to the result thereof, the antibodies may be subjected to the following treatment.

For example, the prepared P03 purified polyclonal antibodies may contain, in addition to P03-specific polyclonal antibodies, polyclonal antibodies binding to at least one peptide selected from P02 peptide and P04 peptide, for example, P02 peptide or P04 peptide.

In some embodiments of the present invention, the obtained P03 purified polyclonal antibodies may be further subjected to a treatment that eliminates antibodies binding to P04 peptide or preferably antibodies binding to P02 peptide and P04 peptide. Examples of the treatment that eliminates antibodies binding to the peptides include purification using an affinity matrix. In more detail, for example, when the antibody contains antibodies binding to P04 peptide, P04 peptide-immobilised column is used for the affinity matrix. As P04 peptide binds to the column through an SH group, cysteine may be linked at the N- or C-terminal. Preferably, the P04 peptide-immobilised column is a column to which both P04 peptide having cysteine linked at N-terminal thereof and P04 peptide having cysteine linked at C-terminal thereof are linked. By carrying out purification using such a column, antibodies binding to P04 peptide may be eliminated from P03 purified polyclonal antibodies. When antibodies also contain antibodies binding to P02 peptide, a P02 peptide-immobilised column may be used for purification in a similar manner as above. Accordingly, anti-presepsin polyclonal antibodies specifically binding to P03 peptide (referred to as "P03-specific polyclonal antibodies") may be obtained from P03 purified polyclonal antibodies.

In other embodiments of the present invention, the obtained P03 purified polyclonal antibodies may be further subjected to a treatment that reduces a binding activity of antibodies binding to P04 peptide or preferably a treatment that reduces a binding activity of antibodies binding to P02 peptide and antibodies binding to P04 peptide. Examples of the treatment that reduces a binding activity of antibodies binding to P04 peptide include a treatment in which P04 peptide is added to P03 purified polyclonal antibodies to allow antigen-antibody reaction and a binding activity of antibodies binding to P04 peptide is blocked. A treatment that reduces a binding activity of antibodies binding to P02 peptide may also be carried out in a similar manner as above. Accordingly, a binding activity of antibodies binding to P04 peptide or preferably a binding activity of antibodies binding to P02 peptide and antibodies binding to P04 peptide in P03 purified polyclonal antibodies may be reduced.

An antigen binding fragment may be prepared from the thus produced polyclonal antibodies according to a well-known method.

Among antigen binding fragments, Fab indicates an antibody fragment having an antigen binding activity in which about a half of the H chain at the N-terminal side and an entire L chain are linked via a disulphide bond. Fab may be prepared by, for example, treating polyclonal IgG antibodies with a protease papain to fragment the antibodies and purifying, if necessary, according to a well-known method.

F(ab')$_2$ is Fab linked with a disulphide bond of a hinge region. F(ab')$_2$ may be prepared by treating polyclonal IgG antibodies with protease pepsin to fragment the antibodies and purifying, if necessary, according to a well-known method.

Fab' is an antibody fragment having an antigen binding activity obtained by digesting the disulphide bond of a hinge region of F(ab')$_2$. Fab' may be prepared by, for example, treating F(ab')$_2$ with a reducing reagent dithiothreitol to digest the disulphide bond of a hinge region and purifying, if necessary, according to a well-known method.

3. Method for Measuring Presepsin

The present invention provides a method (referred to as the "measurement method of the present invention") for immunologically measuring presepsin by using the antibodies of the present invention, wherein the method includes the step of exposing the antibodies of the present invention to a sample containing presepsin. As used herein, the term "measurement" may be interchangeably used with such terms as "detection", "quantification", "assay" and the like and is used to include the meanings of quantitative and qualitative determinations. Measurement of presepsin is carried out preferably in vitro.

As presepsin is a known marker for detection of sepsis, the method may be regarded as a method for detecting sepsis, comprising the step of exposing the antibodies of the present invention to a sample containing presepsin.

Namely, the method may be regarded as a method for detecting sepsis or a method for assisting detection or diagnosis of sepsis, the method comprising 1) the step of measuring a presepsin concentration in a sample from a subject by using the antibodies of the present invention, and 2) the step of comparing the presepsin concentration obtained in 1) with a cut-off value in order to judge whether or not the concentration is higher than the cut-off value. The cut-off value is 314 to 600 pg/mL, preferably 400 to 580 pg/mL, more preferably 450 to 550 pg/mL and even more preferably 500 pg/mL.

In the present invention, "detection of a disease" may be understood as "assist of detection of a disease" or "assist of diagnosis of a disease".

The antibodies may also be used for detection or evaluation of at least one disease selected from such as, discrimination between sepsis and systemic inflammatory response syndrome (SIRS), risk assessment of severity of sepsis, prognosis prediction of sepsis (mortality prediction), the assessment of the degree of septic severity, detection of surgical site infection, detection of disseminated intravascular coagulation (DIC), detection of infectious DIC, detection of heart disease, detection of respiratory infection associated with bacterial infection, detection of inflammatory bowel disease (Crohn's disease, ulcerative colitis), detection of febrile neutropenia (FN), detection of hemophagocytic syndrome (HPS) and evaluating the function of phagocytes.

The term "surgical site infection" as used herein means infectious diseases which are caused after surgery, and includes all infections due to surgery and adjuvant therapies needed therefor. The surgical site infection includes all diseases diagnosed as surgical site infection based on the Guideline for prevention of surgical site infection, 1999 (CDC).

As for heart disease, for example, includes acute coronary syndrome (ACS), acute heart failure, acute decompensated heart failure (ADHF), chronic heart failure, coronary artery disease, angina, myocardial infarction, ischaemic stroke, cerebral haemorrhage and transient ischaemic attack.

Respiratory infection associated with bacterial infection may be lower respiratory tract infection or pneumonia. Lower respiratory tract infection includes acute lower respiratory tract infection and chronic lower respiratory tract infection. Acute lower respiratory tract infection includes acute tracheitis, acute bronchitis and acute bronchiolitis, and most of them occur due to the spread of viral infection from the upper respiratory tract to the lower respiratory tract and in some of these diseases, secondary infection by bacteria then takes place. If signs of bacterial secondary infection have been observed, administration of antibiotics may be adapted. Chronic lower respiratory tract infection is a pathological condition in which persistent bacterial infection has been established at the lower respiratory tract having organic disorders due to bronchiectasis or chronic obstructive pulmonary disease, and includes persistent infection and acute exacerbation. Diseases causing organic disorders to the lower respiratory tract include bronchiectasis, chronic obstructive pulmonary disease, chronic bronchitis, diffuse panbronchiolitis, obsolete pulmonary tuberculosis, pneumoconiosis, nontuberculous mycobacterial infection, allergic bronchopulmonary aspergillosis, pulmonary fibrosis, chronic bronchial asthma and the like. For both persistent infection and acute exacerbation, administration of antibiotics is applied. Pneumonia includes community-acquired pneumonia and hospital-acquired pneumonia. Preferably, pneumonia is community-acquired pneumonia.

Evaluating the function of phagocytes includes (a) measurement of phagocytic ability of neutrophils, granulocytes and/or leukocytes, (b) evaluation of immune function by measuring phagocytic ability of neutrophils, granulocytes and/or leukocytes, (c) quality evaluation of implantable cells upon autologous cell transplantation or allogeneic cell transplantation, (d) detection of a disease associated with phagocytosis by phagocytes and the like. Examples of the disease associated with phagocytosis by phagocytes include autoimmune diseases, rheumatoid arthritis, breast inflammation, gout, glomerulonephritis, ulcerative colitis, Mediterranean fever, otitis media, rhinitis, pneumonia, tuberculosis, cystitis, amniotic fluid infection and pyospermia. The sample used in detecting the disease associated with phagocytosis of phagocytes is body fluids such as tissue fluid, lymph, synovial fluid, milk, cerebrospinal fluid, pus, saliva, lacrimal fluid, mucus, nasal discharge, sputum, urine, peritoneal fluid, amniotic fluid and semen, and as well as lavage fluids obtained after lavage of nasal cavity, bronchus, lung, skin, peritoneal cavity, various organs, joints, bones and the like.

Examples of the method for immunologically measuring presepsin by using the antibodies of the present invention include enzyme immunoassay ((hereinafter also referred to as EIA or ELISA), chemiluminescent enzyme immunoassay (CLEIA), chemiluminescent immunoassay (CLIA), fluorescent antibody method (FAT), fluorescent enzyme immunoassay (FEIA), electro chemiluminescence immunoassay (ECLIA), radioimmunoassay (RIA), immunochromatography, agglutination method, competitive assay and the like, but not limited thereto. In the present invention, either of the direct method and indirect method may be used. A sensitisation method in which detection is carried out after formation of biotin-avidin (streptavidin) complexes may also be used.

EIA is one of immunoassays using an enzyme-labelled antibody and includes a direct method and an indirect method. Preferred examples thereof include sandwich ELISA (enzyme-linked immunosorbent assay).

Sandwich ELISA is a method in which the measurement is performed by using two or more antibodies with different antigen recognition sites and by forming antibody-antigen-antibody complexes with an antigen to be detected being positioned between two kinds of antibodies, and one of the antibodies being preliminarily immobilised on a solid phase.

Chemiluminescent enzyme immunoassay (CLEIA) is a method in which an antigen in a sample is reacted with an antibody immobilised to magnetic particles or beads, followed by a reaction with an enzyme-labelled antibody, washing (B/F separation), enzyme reaction by addition of a chemiluminescence substrate and measurement of the intensity of luminescence.

For example, an antigen in a sample may be reacted with an antibody conjugated with biotin in a liquid phase, the antibody may be trapped by magnetic particles linked with streptavidin and an enzyme-labelled antibody may be allowed to react after washing (B/F separation), followed by the similar treatment as above.

When an alkaline phosphatase (ALP) is used as the labelling enzyme, it is preferable that the chemiluminescence substrate used is CDP-Star™, AMPPD™ or CSPD™. When the labelled enzyme is HRP, luminol is preferably used as a chemiluminescence substrate.

Generally, detection sensitivity is said to be high in the order of chemiluminescence>fluorescence>absorbance (colouration), and a measurement method may be selected according to a desired sensitivity.

Chemiluminescent immunoassay (CLIA) is a method in which an antigen in a sample is reacted with an antibody immobilised to magnetic particles or the like, followed by reaction with an antibody labelled with a chemiluminescence substance, washing (B/F separation) and measurement of the intensity of luminescence. As the labelling substance, acridinium or the like is used.

Fluorescent enzyme immunoassay (FEIA) is a method in which an antigen in a sample is reacted with an immobilised antibody, followed by reaction with an enzyme-labelled antibody, washing (B/F separation), enzyme reaction by addition of a fluorescence substrate and measurement of the intensity of fluorescence. As the labelling enzyme, HRP, ALP or the like is used. It is preferable that Amplex™ Red or the like is used as a fluorescence substrate when the labelling enzyme is HRP, and 4-MUP (4-Methylumbelliphenyl phosphate), AttoPhos™ or the like is used as a fluorescence substrate when the labelling enzyme is ALP.

Electro chemiluminescence immunoassay (ECLIA) is a method in which an antigen in a sample, an antibody immobilised to magnetic particles and an antibody labelled with an electro chemiluminescence substance are allowed to react, followed by washing (B/F separation) and measurement of the intensity of electric energy luminescence. Ruthenium or the like is used as a labelling substance. When $Ru(bpy)_3$ or the like is used as a labelling substance, excitation luminescence is repeated due to oxidation based on charging an electrode and reduction reaction by tripropylamine (TPA) or the like.

Radioimmunoassay ((RIA) is a measurement method using a substance labelled with a radioisotope. For example, after reaction of an antigen in a sample and an antibody immobilised to beads or the like, an antibody labelled with a radioisotope (125I or the like) is allowed to react and the dose of 125I may be measured after washing (B/F separation).

Immunochromatography is an immunoassay based on a capillary action of a substance to be detected migrating on a test strip while dissolving a reagent. It is a method in which an immunocomplex is formed among three substances, that is, an antigen in a sample, a labelled antibody on a test strip, and a capturing antibody, and the colour of the labelled product is observed. As the label of an antibody, colloidal gold, enzymes, fluorescence substances or the like is used. When an enzyme-labelled antibody is used, a substrate for the enzyme is applied on a test strip for colour development.

A flow through method is a method in which on an insoluble carrier which is a membrane, an antigen to be detected together with a solution in a specimen forms an antibody-antigen-antibody complex. At the time, a substance which is not immobilised on the membrane perpendicularly passes through the membrane from the surface to the back surface of membrane, and it is removed.

The agglutination method is a method in which an antigen in a sample is reacted with an antibody in a reagent and agglutination thereof is observed. The method includes a method without using a solid phase, particle agglutination (PA) method in which artificially prepared particles are used as a solid phase, and PA including latex agglutination (LA) method in which latex particles are used.

In the competitive assay, for example, an antibody is bound to a solid phase and is simultaneously reacted with a sample for test and a certain amount of a labelled antigen, and thus an amount of antigen in the sample may be measured from the amount of the bound labelled product.

The antibodies of the present invention are preferably used for the above measurement methods.

A sample used for presepsin measurement is not particularly limited but is preferably an aqueous sample. Examples thereof include body fluids such as blood (whole blood, blood plasma, blood serum, etc.), urine, tissues fluid, lymph fluid, synovial fluid, milk, cerebrospinal fluid, pus, saliva, lacrimal fluid, mucus, nasal discharge, sputum, peritoneal fluid, amniotic fluid and semen, and as well as lavage fluids obtained after lavage of nasal cavity, bronchus, lung, skin, peritoneal cavity, various organs, joints, bones and the like, cell culture supernatants, column eluents and the like. Those samples can be used for measurement either directly or after dilution or extraction with various buffers followed by concentration.

Furthermore, in case of using whole blood as a sample, the whole blood sample be analyzed within 72 hours, 48 hours, 24 hours, 12 hours, 6 hours or 4 hours after the whole blood sample is collected. Collecting whole blood sample may be performed by using an EDTA blood collection tube or a heparin blood collection tube. Preferably, the whole blood sample is analysed within 6 hours after it is collected into an EDTA blood collection tube or within 4 hours after it collected into a heparin blood collection tube.

4. Kit for Measuring sCD14-ST

The present invention provides a kit (referred to as the "measurement kit of the present invention") for measuring presepsin including the antibodies of the present invention as an essential constituent.

The measurement kit of the present invention preferably includes an auxiliary reagent for measuring presepsin. Examples of the auxiliary reagent include a primary antibody, a secondary antibody, a labelled antibody, a labelling enzyme, a labelling substance such as colloidal gold, a chromogenic substrate, a fluorescence substrate (such as Amplex™ Red, AttoPhos™ and 4-MUP), a chemiluminescence substrate (such as luminol, CDP-Star™, AMPPD™ and CSPD™), a specifically binding substance such as biotin-streptavidin, an insoluble carrier, a blocking agent, a diluent, a washing solution, a standard substance and the like without limitation.

The measurement kits of the present invention are appropriately combined and used according to the presepsin measurement method.

The primary antibody is preferably an antibody binding to presepsin and is more preferably an antibody recognising an epitope different from the one recognised by the antibodies of the present invention. Examples thereof include F1106-13-3 antibody and F1031-8-3 antibody described in Example 3 of WO2004/044005.

Either of the antibodies of the present invention and the primary antibody may be labelled. If neither of the antibodies of the present invention or the primary antibody is labelled, a labelled secondary antibody may be used.

Examples of the insoluble carrier include magnetic particles, beads, glass, cellulose, nitrocellulose, porous synthetic polymers, glass fibres, polyacrylamide, nylon, polystyrene, polyvinyl chloride, polypropylene, plastic plates, latex particles, non-woven fabrics, filter paper and the like.

A label for an antibody may preferably be enzymes such as peroxidase (HRP), alkaline phosphatase (ALP) and β-galactosidase, colloidal gold and the like without limitation.

For example, when HRP is used, a chromogenic substrate may be 3,3',5,5'-tetramethylbenzidine (TMB), o-phenylenediamine (OPD) or the like. When ALP is used, a chromogenic substrate may be p-nitrophenylphosphate (pNPP) or the like. Examples of a chromogenic substrate when β-galactosidase is used include o-nitrophenyl-β-D-galactopyranoside (ONPD) and the like.

For example, a measurement kit for sandwich ELISA may contain the antibodies of the present invention and a primary antibody (either of the antibody may be labelled with an enzyme), a chromogenic substrate, a diluent, a standard substance and the like. When neither of the antibodies of the present invention or the primary antibody is labelled, the kit may also contain a labelled secondary antibody.

A measurement kit for chemiluminescent enzyme immunoassay (CLEIA) may contain, for example, an antibody immobilised to magnetic particles or the like, an enzyme-labelled antibody, a chemiluminescence substrate, a diluent, a washing solution and the like.

A measurement kit for fluorescent enzyme immunoassay (FEIA) may contain, for example, an antibody immobilised to magnetic particles or the like, an enzyme-labelled antibody, a fluorescence substrate, a diluent, a washing solution and the like.

A measurement kit for electro chemiluminescence immunoassay (ECLIA) may contain, for example, biotinylated antibody, a Ru(bpy)$_3$-labelled antibody, streptavidin-coated magnetic particles, tripropylamine and the like.

A measurement kit for immunochromatography is a test strip including a sample addition unit, a reagent unit, a detection unit and an absorbent unit which are provided so that a liquid sample added to a test addition unit migrates through the units in the above order. For example, the reagent unit may be impregnated with a labelled second antibody and an insoluble carrier bound to a first antibody may be provided at the detection unit.

The test strip may be exemplified by one containing a porous carrier and the like. Examples of the porous carrier include nitrocellulose, cellulose, cellulose derivatives, nylon, nylon fibres, glass fibres, porous synthetic polymers and the like. The absorbent unit may be absorbent polymers such as sponge made with water-absorbing materials, cellulose filters, filter paper and the like.

As it is reported that sepsis patients have a characteristic increased blood presepsin concentration, the presepsin measurement kit of the present invention may be a kit for detecting sepsis or a kit for assisting detection or diagnosis of sepsis.

The measurement kit of the present invention may also be used as a diagnostic agent for sepsis or an auxiliary agent for diagnosing sepsis. When the presepsin measurement kit is used for a purpose of detection of sepsis or the like, it is determined that a subject has a possibility of sepsis when the presepsin concentration in a sample from the subject measured using the antibodies of the present invention is higher than a cut-off value, thereby this can assist the detection or diagnosis. The cut-off value is 314 to 600 pg/mL, preferably 400 to 580 pg/mL, more preferably 450 to 550 pg/mL and further more preferably 500 pg/mL.

In addition, a presepsin measurement kit may be used for detection or evaluation, for example, at least one disease selected from such as, distinction of sepsis from systemic inflammatory response syndrome (SIRS), risk assessment of severity of sepsis, prognosis assisting detection of sepsis (mortality prediction), the assessment of the degree of septic severity, detection of surgical site infection, detection of disseminated intravascular coagulation (DIC), detection of infectious DIC, detection of heart disease, detection of respiratory infection associated with bacterial infection, detection of inflammatory bowel disease (Crohn's disease, ulcerative colitis), detection of febrile neutropenia (FN), detection of hemophagocytic syndrome (HPS) and f evaluating the function of phagocytes. The presepsin measurement kit may be a kit for at least one detection or evaluation of diseases as described above.

5. Method for Therapy of Sepsis Patients

The present invention provides a method of treating a sepsis patient comprising sepsis treatment on a subject who has been undergone a method for assisting detection of sepsis by using the antibodies of the present invention.

The method for assisting detection of sepsis is as described above. The sepsis therapy includes, for example, administration of antibacterial agents or steroids, vasopressors, fluid replacement, administration of oxygen, artificial respiration control, continuous hemodiafiltration, plasmapheresis and the like, but it is not particularly limited.

6. Method for Screening Test Drugs (or Therapeutic Drugs)

The present invention provides a method for screening a test drug (or a therapeutic drug), comprising the step of determining a presepsin concentration in a sample from a subject administered with the test drug (or the therapeutic drug), using the antibodies of the present invention or the measurement kit of the present invention. A disease to which a test drug is targeted not particularly limited as far as it is a disease in which the presepsin concentration in a sample from a subject is increased. Preferably, the presepsin concentration in a sample from a subject is compared between before and after a test drug administration to determine whether or not the presepsin concentration after a test drug administration is reduced in comparison with before administration. Alternatively, whether or not the presepsin concentration in a sample from a subject after a test drug administration is reduced compared to the level of normal person is determined.

In one embodiment, the method for screening a test drug comprises the following step:
1) a step of determining the presepsin concentration in a sample from a subject administered with a test drug.

7. Method for Screening Anti-Presepsin Polyclonal Antibodies

The present invention provides a method for screening antibodies, to obtain anti-presepsin polyclonal antibody useful for presepsin measurement in a sample, in which the method includes at least the following steps:
1) the step of obtaining candidate of anti-presepsin polyclonal antibodies; and
2) the step of constructing a presepsin measurement system with the candidate antibodies and selecting antibodies in a reaction system for competitive reaction of a peptide (P03 peptide) comprising an amino acid sequence of SEQ ID NO: 1 so as to inhibit binding between the antibodies and presepsin, the selected antibodies competitively inhibiting binding of the antibodies and presepsin by 30% or more, and
in a reaction system for allowing competitive reaction of a peptide (P05 peptide) comprising an amino acid sequence of SEQ ID NO: 9 so as to inhibit binding between the antibodies and presepsin, the selected antibodies competitively inhibiting binding of the antibodies and presepsin by less than 30%.

The competitive inhibition assay may be carried out according to the description in Example 3.

Preferably, the method may further include the step of selecting antibodies having competitive inhibition by P01 peptide, P02 peptide, P04 peptide, P06 peptide, P07 peptide and/or P08 peptide of less than 30%. The peptides may be appropriately selected.

All references, published patent applications, published granted patent applications and other patent references cited herein are incorporated herein by reference.

The present invention is more specifically described hereinafter by way of Examples. It should not be understood that the present invention is limited to Examples.

EXAMPLES

Example 1: Preparation of Polyclonal Antibodies Specifically Purified with S68 Peptide or P03 Peptide Rabbit anti-S68 peptide polyclonal antibodies obtained by immunising rabbits with an immunogen S68 peptide were specifically purified by using affinity columns to which P03 peptide (SEQ ID NO: 1) and S68 peptide (SEQ ID NO: 2) were immobilised, respectively.

1-1: Preparation of Rabbit Anti-S68 Peptide Polyclonal Antibodies

According to the method disclosed in Example 1 of WO2004/044005, rabbits were immunised with an immunogen S68 peptide-KLH. Thereafter, antiserum was prepared according to a conventional method and 3 lots of purified IgG fractions (A, B and C) were prepared by ammonium sulphate precipitation and Protein A purification (Prosep-A, Millipore Corporation).

1-2: Preparation of P03 Peptide-Immobilised Affinity Column and S68 Peptide-Immobilised Affinity Column According to the manual, 3.0 mL of SulfoLink Coupling Gel (ThermoFisher Scientific) was packed to a column which was then washed with 6 column volumes of 50 mM Tris, 5 mM EDTA (pH 8.5). The bottom of the column was closed with a lid. S68 peptide (2.5 mg) having cysteine linked at the N-terminal and P03 peptide (3.0 mg, a mixture of equal amounts of SEQ ID NOs: 4 and 5) having cysteine linked at N- or C-terminal were respectively dissolved into 50 mM Tris, 5 mM EDTA (pH 8.5) at 1 mg/mL.

P03 peptide having cysteine linked at the N-terminal (SEQ ID NO: 4: CKRVDADADPR).

P03 peptide having cysteine linked at the C-terminal (SEQ ID NO: 5: KRVDADADPRC).

The prepared peptide solutions were added to the gel of each column and the top of each column was sealed. The columns were mixed by inverting at room temperature for 15 minutes and incubated at room temperature for 30 minutes. The lids at the top and bottom of the columns were removed and reaction solutions were collected by natural dripping. The gel was washed with 3 gel volumes of 50 mM Tris, 5 mM EDTA (pH 8.5) followed by blocking of unreacted active groups with a solution containing 50 mM cysteine. After the reaction, the gel was washed with 16 gel volumes of 1 M NaCl and 16 gel volumes of phosphate buffer (PBS, pH 7.4). The gel was stored in a refrigerator after addition of 1 M NaCl/PBS solution.

1-3: Preparation of Specifically Purified Antibodies

S68 peptide-immobilised gel and P03 peptide-immobilised gel prepared in 1-2 were respectively injected in 1 mL columns which were then washed with PBS and equilibrated. 3 lots of purified IgG fractions (50 mg each) obtained in 1-1 were applied to two different peptide-immobilised affinity columns at a flow rate of 0.5 mL/min and non-adsorbed fraction was washed with PBS. Thereafter, the columns were eluted with 0.1 M Glycine-HCl buffer (pH 2.5) and peak fractions were collected. The obtained eluted fractions were neutralised, concentrated and then dialysed against PBS (pH 7.4). The purity of obtained antibodies was verified on SDS-PAGE, and a single band at around 150 kDa was observed. The protein concentration was measured with DC Protein Assay (Bio-Rad Laboratories, Inc.). The results of the protein concentration of the prepared antibodies are shown in Table 1. S68-A, S68-B and S68-C indicate antibodies obtained by specific purification on the S68 peptide immobilised affinity column and P03-A, P03-B and P03-C indicate antibodies obtained by purification on the P03 peptide-immobilised affinity column.

TABLE 1

| Antibody | Protein concentration (mg/mL) |
| --- | --- |
| S68-A | 0.47 |
| S68-B | 0.28 |
| S68-C | 0.44 |
| P03-A | 0.24 |
| P03-B | 0.23 |
| P03-C | 0.11 |

Example 2: Evaluation of Reactivity with Presepsin

By using six different specifically purified antibodies prepared in Example 1, sandwich ELISA systems were prepared and a standard presepsin product (rsCD14-ST disclosed in Example 16 of WO2005/108429) was measured and the reactivity of these antibodies were evaluated. (Hereinafter, the antibodies obtained by specific purification on the P03 peptide-immobilised affinity column are referred to as "P03 purified polyclonal antibodies" and the antibodies obtained by specific purification on the S68 peptide-immobilised affinity column are referred to as "S68 antibodies".)

2-1: Preparation of Antibody-Immobilised Plates

Six antibodies prepared in Example 1 were respectively diluted in PBS (pH 7.4) to 5 µg/mL and dispensed to immuno plates (MAXISORP, C8 plate, Nunc). The plates were sealed and incubated at 4° C. overnight. Next day, the plates were washed five times with cold PBS (pH 7.4) and added with 200 mL of blocking solution to prepare the plates onto which respective antibodies were immobilised.

2-2: Comparison of Reactivity of Specifically Purified Antibodies by Sandwich ELISA The standard presepsin product was diluted to 500 pg/mL in a sample diluent (D-PBS (pH 7.4) containing 0.1% BSA). To each plate prepared in 2-1, 50 µL per well of sample diluent (corresponding to 0 pg/mL of standard presepsin product) or 500 pg/mL of standard presepsin product was added and the reaction was allowed to proceed on a shaker (TAITEC bioShaker M-BR-022UP) at 500 rpm and 25° C. for 1 hour. After the completion of the reaction, the plates were washed five times with saline containing 0.05% Tween 20 on a plate washer (Biotec MW-96AR, Nunc-Immuno-Wash) followed by addition of 50 µL per well of a solution of a peroxidase-labelled F1106-13-3 antibody (disclosed in Example 3 of WO2004/044005) diluted in a labelled antibody diluent to 0.125 µg/mL. After the reaction at 25° C. and 500 rpm for 2 hours, the plates were similarly washed five times, a tetramethylbenzidine solution (TMB, BioFx) was added to each well and the reaction was allowed to proceed at room temperature for 20 minutes. To each well, 50 µL of 1 M sulphuric acid solution was added to terminate the reaction and absorbance was measured at 450 nm/650 nm on a plate spectrophotometer (CORONA ELECTRIC MTP-300). The absorbance of the antibodies when 0 pg/mL or 500 pg/mL of standard presepsin product was added is shown in Table 2.

As a result, the S/N ratio (Absorbance at addition of 500 pg/mL of standard presepsin product/Absorbance of 0 pg/mL of standard presepsin product) determined based on the absorbance was 44 to 57 for the P03 purified polyclonal antibodies, while 17 to 35 for the S68 antibodies. It was found that the S/N ratio of the P03 purified polyclonal antibodies was about 2 to 3 times higher than that of the S68 antibodies. As a result, it was found that even if the antibodies were derived from the same polyclonal antibodies, purification with the P03 peptide-immobilised affinity column could prepare antibodies having higher reactivity to presepsin than purification with the S68 peptide-immobilised column.

TABLE 2

| Antibody | Absorbance (presepsin 0 pg/mL) | Absorbance (presepsin 500 pg/mL) | S/N ratio |
| --- | --- | --- | --- |
| S68-A | 0.037 | 1.301 | 35 |
| S68-B | 0.047 | 0.784 | 17 |
| S68-C | 0.040 | 0.810 | 20 |
| P03-A | 0.070 | 3.078 | 44 |
| P03-B | 0.057 | 2.760 | 48 |
| P03-C | 0.045 | 2.549 | 57 |

Example 3: Evaluation of Specificity: Peptide Competitive Inhibition Reaction

In order to evaluate the specificity of six different antibodies prepared in Example 1, sandwich ELISA prepared in Example 2 was used and partial peptides derived from S68 peptide (10 amino acids each, see Table 3) were added to the reaction respectively of the antibodies with presepsin to perform a competitive inhibition assay.

3-1: Preparation of Peptides

Eight peptides were synthesized with P01 peptide comprising 10 amino acids including 3 N-terminal amino acids of S68 peptide and the other peptides comprising 3 amino acids shifted therefrom to the C-terminal side (Table 3). The synthesised peptides were diluted in PBS (pH 7.4) to 20 mg/mL to prepare inhibiting peptides.

TABLE 3

| Peptide | Position of amino acids in SEQ ID NO: 3 | Amino acid sequence | SEQ ID NO: |
| --- | --- | --- | --- |
| S68 | Position 53 to position 68 | rvdadadprqyadtvk | 2 |
| P01 | Position 46 to position 55 | nlepflkrvd | 6 |
| P02 | Position 49 to position 58 | pflkrvdada | 7 |
| P03 | Position 52 to position 61 | krvdadadpr | 1 |
| P04 | Position 55 to position 64 | dadadprqya | 8 |
| P05 | Position 58 to position 67 | adprqyadtv | 9 |
| P06 | Position 61 to position 70 | rqyadtvkal | 10 |
| P07 | Position 64 to position 73 | adtvkalrvr | 11 |
| P08 | Position 67 to position 76 | vkalrvrrlt | 12 |

3-2: Evaluation of Specificity

The standard presepsin product was diluted in PBS (pH 7.4) to prepare a standard product of 400 pg/mL. As a control, PBS (pH 7.4) without peptide was used. According to the method described in Example 2, 25 µL of the inhibiting peptide prepared in 3-1 and 25 µL of the standard presepsin product were added to the plates prepared with the respective specifically purified antibodies and allowed to react at 25° C. and 500 rpm for 1 hour. After washing the plates, a labelled antibody was added and allowed to react in a similar manner. From the obtained absorbance, a peptide having the absorbance reduced by 30% or more compared to that of the control was judged to have a binding activity.

As a result, the S68 antibodies contained antibodies reacting with P01 to P05 peptides, while 2 lots of the P03 purified polyclonal antibodies contained antibodies reacting with P03 peptide and P04 peptide and 1 lot of the P03 purified polyclonal antibodies contained antibodies reacting with P02 peptide, P03 peptide and P04 peptide. The results are shown in Table 4.

TABLE 4

| Inhibiting peptide | Antibody | | | | | |
|---|---|---|---|---|---|---|
| | S68-A | S68-B | S68-C | P03-A | P03-B | P03-C |
| P01 | − | + | − | − | − | − |
| P02 | − | + | + | − | + | − |
| P03 | + | + | + | + | + | + |
| P04 | + | + | + | + | + | + |
| P05 | + | + | + | − | − | − |
| P06 | − | − | − | − | − | − |
| P07 | − | − | − | − | − | − |
| P08 | − | − | − | − | − | − |
| S68 | + | + | + | + | + | + |

Residual reactivity (%)
−: Above 70%,
+: at or below 70%

Example 4: Comparison of Cross Reaction with High Molecular Weight sCD14 in Blood Six antibodies obtained in Example 1 were measured for the cross reaction with high molecular weight sCD14 in blood by sandwich ELISA. From the results in Example 3, it was found that the P03 purified polyclonal antibodies contained antibodies binding to P03 peptide and P04 peptide. Thus, in ELISA using the P03 purified polyclonal antibodies, a final concentration 20 μg/mL of P04 peptide was added to diluents of high molecular weight sCD14 in blood and standard presepsin product in order to block the binding activity of antibodies binding to P04 peptide, thereby evaluating the antibodies (P03-specific polyclonal antibodies) specifically binding to P03 peptide.

4-1: Preparation of Blood High Molecular Weight sCD14

High molecular weight sCD14 in blood was prepared as follows. Normal human serum was applied to a column to which an anti-CD14 antibody (F1024-1-3: disclosed in Example 2 of WO01/072993) was immobilised and CD14 was absorbed to prepare CD14 absorbed human serum. CD14 absorbed human serum and normal human serum were measured for the concentration of high molecular weight sCD14 in blood with the CD14 ELISA kit (R&D Systems, Inc., #DC140). Normal human serum had a concentration of high molecular weight sCD14 in blood of 1603 ng/mL and CD14 absorbed human serum had 21 ng/mL. The sera were mixed to prepare a series of dilution of high molecular weight sCD14.

4-2: Measurement of Cross Reaction

A series of dilution of blood high molecular weight sCD14 (21 to 1603 ng/mL) was prepared, diluted 20 times in a diluent and the absorbance was measured by ELISA using the respective antibodies according to the method described in Example 2. The standard presepsin products (0 to 500 pg/mL) were also measured and a presepsin standard curve was prepared based on the obtained absorbance. The absorbance of a sample containing high molecular weight sCD14 in blood (1603 ng/mL) was measured by ELISA using the antibodies, plotted on the presepsin standard curve and the concentration corresponding to the absorbance was determined. The cross reaction was calculated by dividing the obtained concentration by the concentration (as measurement was carried out after 20 times dilution, 80 ng/mL was used) of high molecular weight sCD14 in blood used for the measurement.

Cross reaction (%)=(Concentration determined by plotting the absorbance of the sample containing high molecular weight sCD14 in blood measured by the antibodies on the presepsin standard curve/Concentration of high molecular weight sCD14 in blood used for the measurement)×100(%)

The results are shown in Table 5.

As a result, it was found that in the ELISA assay system using the P03-specific polyclonal antibodies, the cross-reaction with high molecular weight sCD14 in blood was at or below the detection limit and the P03-specific polyclonal antibodies had rare cross-reaction with high molecular weight sCD14 in blood. From the results, it was demonstrated that ELISA prepared with P03-specific polyclonal antibodies allows measurement of presepsin with higher accuracy than ELISA using S68 antibodies.

TABLE 5

| | Antibody (cross-reaction %) | | | | | |
|---|---|---|---|---|---|---|
| | S68-A | S68-B | S68-C | P03-A | P03-B | P03-C |
| High molecular weight sCD14 in blood (1603 ng/mL) | 0.05 | 0.03 | 0.02 | ND | ND | ND |
| Average (%) | | 0.03 | | | At or below detection limit | |

(ND: at or below detection limit)

Example 5: Measurement of Samples from Sepsis Patients Having Known Concentration By using ELISA prepared with six different antibodies obtained in Example 1, 22 samples from sepsis patients having known concentration were measured and correlation analysis was performed. Presepsin of the samples having known concentration were measured with the presepsin measurement kit using S68 antibodies. According to Example 4, a final concentration 20 μg/mL of P04 peptide was added to diluents of the standard presepsin product and patient samples in order to block antibodies binding to P04 peptide in the P03 purified polyclonal antibodies, thereby evaluating P03-specific polyclonal antibodies.

5-1: Measurement of Sepsis Patient Samples by Sandwich ELISA

By using sandwich ELISA described in Example 2, standard presepsin products (0 to 500 pg/mL, 8 points with n=2 each) and sepsis patient samples diluted 20 times in a diluent (n=2) were measured. A standard curve was prepared from the absorbances of the standard presepsin products using SoftMax Pro (Molecular Devices, Llc.) and the concentration of the each sample was calculated. Measured values having a coefficient of variance (CV) of 30% or more were excluded from the analysis.

5-2: Correlation Analysis of Measured Results

With the measured values obtained in 5-1 and known concentration, correlation analysis was performed on Excel 2007 to determine regression lines. The regression lines prepared for P03-specific polyclonal antibodies (3 lots) are shown in FIGS. 1 to 3. The results of the regression analysis are shown in Table 6.

As a result, the coefficient of variance (CV) of the slopes of the regression lines for 3 lots of S68 antibodies was 20%, while the CV for 3 lots of P03-specific polyclonal antibodies was 10.6%. By using the P03-specific polyclonal antibodies, it is suggested that a presepsin measurement kit may be stably prepared with less variation in measured values between lot-to-lot differences of antibodies.

TABLE 6

| | Antibody | | | | | |
|---|---|---|---|---|---|---|
| | S68-A | S68-B | S68-C | P03-A | P03-B | P03-C |
| Slope | 2.38 | 2.95 | 3.56 | 1.58 | 1.51 | 1.84 |
| R2 | 0.956 | 0.935 | 0.959 | 0.969 | 0.926 | 0.981 |
| Coefficient of correlation | 0.978 | 0.967 | 0.979 | 0.984 | 0.962 | 0.990 |
| CV of slope | | 20% | | | 10.6% | |

Example 6: Preparation of P03-Specific Polyclonal Antibodies

From the results of Example 3, it was found that antibodies prepared with the P03 peptide-immobilised affinity column contained antibodies binding to P03 peptide and P04 peptide. Thus, by eliminating antibodies binding to P04 peptide from the obtained antibodies, anti-presepsin polyclonal antibodies specifically binding to P03 peptide are prepared. The following method can be applied when antibodies binding to other peptides are eliminated.

6-1: Method of Using P04 Peptide-Immobilised Affinity Column

According to the method described in Example 1, a P04 peptide-immobilised affinity column is prepared with P04 peptide. According to Example 1-3, the IgG fraction obtained in Example 1-1 is applied to the P04 peptide-immobilised affinity column. The antibodies binding to P04 peptide are eliminated by passing through the P04 peptide-immobilised affinity column. The obtained non-adsorbed fraction is purified with the P03 peptide-immobilised affinity column according to the method described in Example 1, thereby obtaining P03-specific polyclonal antibodies.

6-2: Method of Adding P04 Peptide

After adding P04 peptide to the IgG fraction obtained in Example 1-1, purification with the P03 peptide-immobilised affinity column is carried out. By this process, antibodies binding to P04 peptide may be eliminated for purification, thereby obtaining P03-specific polyclonal antibodies.

[Sequence Listing Free Text]

[SEQ ID NO: 1] Amino acid sequence of P03 peptide.
[SEQ ID NO: 2] Amino acid sequence of S68 peptide.
[SEQ ID NO: 3] Amino acid sequence of human full-length soluble CD14.
[SEQ ID NO: 4] Amino acid sequence of P03 peptide having cysteine linked at the N-terminal.
[SEQ ID NO: 5] Amino acid sequence of P03 peptide having cysteine linked at the C-terminal.
[SEQ ID NO: 6] Amino acid sequence of P01 peptide.
[SEQ ID NO: 7] Amino acid sequence of P02 peptide.
[SEQ ID NO: 8] Amino acid sequence of P04 peptide.
[SEQ ID NO: 9] Amino acid sequence of P05 peptide.
[SEQ ID NO: 10] Amino acid sequence of P06 peptide.
[SEQ ID NO: 11] Amino acid sequence of P07 peptide.
[SEQ ID NO: 12] Amino acid sequence of P08 peptide.

The invention claimed is:

1. Anti-presepsin polyclonal antibodies, wherein the antibodies specifically bind to a peptide comprising the amino acid sequence of SEQ ID NO: 1 and are substantially free of polyclonal antibodies that do not bind to the amino acid sequence of SEQ ID NO: 1.

2. An anti-presepsin polyclonal antibodies preparation, wherein a content percentage of anti-presepsin polyclonal antibodies specifically binding to a peptide consisting of the amino acid sequence of SEQ ID NO: 1 in the preparation is higher than a content percentage of the anti-presepsin polyclonal antibodies specifically binding to the peptide consisting of the amino acid sequence of SEQ ID NO: 1 in a S68 antibodies anti-presepsin polyclonal antibodies preparation.

3. The antibodies according to claim 1,
wherein the binding between the anti-presepsin polyclonal antibodies and presepsin is competitively inhibited by 30% or more in a competitive reaction system comprising the amino acid sequence of SEQ ID NO: 1, and wherein the binding between the anti-presepsin polyclonal antibodies and presepsin is competitively inhibited by less than 30% in a competitive reaction system comprising the amino acid sequence of SEQ ID NO: 9.

4. The anti-presepsin antibodies according to claim 1, wherein when the antibodies are used in an ELISA assay system, the ELISA assay system has a lower incidence of cross-reaction with high molecular weight soluble CD14 in human blood than an ELISA assay system using S68 antibodies.

5. The antibodies according to claim 1, wherein measured presepsin concentrations in samples, which concentrations are measured using the anti-presepsin polyclonal antibodies in an ELISA assay system, have a coefficient of variance (CV) of slopes of regression lines being 15% or less with respect to previously known presepsin concentrations of said samples.

6. The anti-presepsin antibodies according to claim 1, wherein the antibodies bind to presepsin at an affinity (KD) of less than $10^{-7}$.

7. The anti-presepsin antibodies according to claim 1, wherein the antibodies are obtained by purifying polyclonal antibodies obtained from a non-human mammal immunised by a peptide, as an immunogen, including amino acid residues from position 1 to position 9 of an amino acid sequence of SEQ ID NO: 2 and including 9 or more consecutive amino acid residues in the amino acid sequence of SEQ ID NO: 2.

8. The anti-presepsin antibodies according to claim 1, obtained by subjecting polyclonal antibodies by a treatment to increase a proportion of antibodies specifically binding to the peptide comprising the amino acid sequence of SEQ ID NO: 1, wherein the polyclonal antibodies are obtained from a non-human mammal immunised by a peptide, as an immunogen, including amino acid residues from position 1 to position 9 of an amino acid sequence of SEQ ID NO: 2 and including 9 or more consecutive amino acid residues in the amino acid sequence of SEQ ID NO: 2.

9. Anti-presepsin polyclonal antibodies obtained by purifying, using a column to which a peptide comprising an amino acid sequence of SEQ ID NO: 1 is immobilised, polyclonal antibodies obtained from a non-human mammal immunised using, as an immunogen, a peptide including amino acid residues from positions 1 to 9 of an amino acid sequence of SEQ ID NO: 2 and including 9 or more consecutive amino acid residues in the amino acid sequence of SEQ ID NO: 2.

10. The antibodies according to claim 9, further subjected to a treatment that eliminates antibodies binding to a peptide comprising an amino acid sequence of SEQ ID NO: 8.

11. The antibodies according to claim 9, further subjected to a treatment that reduces a binding activity of antibodies binding to a peptide comprising an amino acid sequence of SEQ ID NO: 8.

12. A method for producing anti-presepsin polyclonal antibodies, comprising at least the following steps: the step of obtaining polyclonal antibodies from a non-human mammal immunised using a peptide, as an immunogen, including amino acid residues from position 1 to position 9 of an amino acid sequence of SEQ ID NO: 2 and including 9 or more consecutive amino acid residues in the amino acid sequence of SEQ ID NO: 2; and the step of purifying the obtained antibodies using a column to which a peptide comprising an amino acid sequence of SEQ ID NO: 1 is immobilised.

13. The method for producing anti-presepsin polyclonal antibodies according to claim 12, further comprising the step of eliminating antibodies binding to a peptide comprising an amino acid sequence of SEQ ID NO: 8.

14. A method for measuring presepsin, comprising at least the step of exposing the antibodies according to claim 1 to a sample containing presepsin.

15. A kit for measuring presepsin, comprising at least the anti-presepsin antibodies according to claim 1.

16. A kit for detecting sepsis or a kit for assisting detection or diagnosis of sepsis, comprising at least the anti-presepsin antibodies according to claim 1.

17. The anti-presepsin polyclonal antibodies of claim 1, which are free of polyclonal antibodies that do not bind to the amino acid sequence of SEQ ID NO: 1.

18. The anti-presepsin polyclonal antibodies preparation of claim 2, which is substantially free of polyclonal antibodies that do not bind to the amino acid sequence of SEQ ID NO: 1.

19. The anti-presepsin polyclonal antibodies preparation of claim 2, wherein the content percentage of the anti-presepsin polyclonal antibodies specifically binding to the peptide consisting of the amino acid sequence of SEQ ID NO: 1 in the preparation is 50% or more.

20. The anti-presepsin polyclonal antibodies preparation of claim 2, wherein the content percentage of the anti-presepsin polyclonal antibodies specifically binding to the peptide consisting of the amino acid sequence of SEQ ID NO: 1 in the preparation is 70% or more.

* * * * *